US005739132A

United States Patent [19]

Ishida et al.

[11] Patent Number: 5,739,132

[45] Date of Patent: Apr. 14, 1998

[54] PYRIDAZINONE DERIVATIVES AND PROCESSES FOR PREPARING THE SAME

[75] Inventors: Akihiko Ishida, Urawa; Koichi Homma, Tokyo-to; Harumichi Kono; Koji Tamura, both of Omiya; Yasuhiko Sasaki, Urawa, all of Japan

[73] Assignee: Tanabe Seiyaku Co., Ltd., Osaka, Japan

[21] Appl. No.: 767,444

[22] Filed: Dec. 16, 1996

Related U.S. Application Data

[63] Continuation of Ser. No. 83,489, Jun. 30, 1993, abandoned.

[30] Foreign Application Priority Data

| | | | |
|---|---|---|---|
| Jul. 2, 1992 | [JP] | Japan | 4-215354 |
| Jul. 2, 1992 | [JP] | Japan | 4-215355 |

[51] Int. Cl.$^6$ .......... A61K 31/50

[52] U.S. Cl. .......... 514/247; 514/253; 544/238; 544/239; 544/114

[58] Field of Search .......... 514/247; 544/239

[56] References Cited

U.S. PATENT DOCUMENTS

| | | | |
|---|---|---|---|
| 2,712,012 | 6/1955 | Clark et al. | 544/239 |
| 4,374,990 | 2/1983 | Weber et al. | 544/376 |
| 4,820,705 | 4/1989 | Nickl et al. | 514/247 |
| 5,179,018 | 1/1993 | Bogard, Jr. et al. | 530/388.15 |
| 5,409,956 | 4/1995 | Yoshida et al. | 514/239 |
| 5,543,409 | 8/1996 | Ishida | 514/247 |
| 5,605,901 | 2/1997 | Ishida | 514/247 |

FOREIGN PATENT DOCUMENTS

| | | |
|---|---|---|
| 194548A3 | 9/1986 | European Pat. Off. . |
| 0253321A2 | 1/1988 | European Pat. Off. . |
| 0589037A1 | 3/1994 | European Pat. Off. . |
| A3223277 | 10/1991 | Japan . |
| 9215558 | 9/1992 | WIPO . |

OTHER PUBLICATIONS

Dorland's Illustrated Medical Dictionary, 26th Ed., pp. 874 and 1080.

Chem Abstract 108, 186330 (1988).

Chem Abstract V.116, No. 128652V (1992).

*Primary Examiner*—Donald G. Daus

*Attorney, Agent, or Firm*—Birch, Stewart, Kolasch & Birch, LLP

[57] ABSTRACT

Disclosed are a pyridazinone compound represented by the formula:

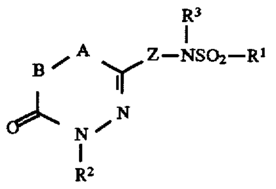

(I)

wherein (1) $R^1$ is a substituted or unsubstituted $C_{1-10}$ alkyl, a $C_{3-6}$ cycloalkyl, a lower alkenyl, a heterocyclic group having N, O or S atom or camphor-10-yl; $R^3$ is hydrogen, a substituted or unsubstituted lower alkyl or a lower alkenyl; or $R^1$ and $R^3$ are bonded at terminal ends thereof to form a lower alkylene; and Z is a group represented by the formula:

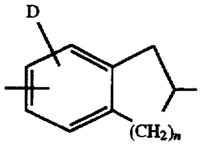

where n is 1 or 2; and D is hydrogen or a halogen; or (2) $R^1$ is a substituted or unsubstituted $C_{1-10}$ alkyl, a substituted or unsubstituted phenyl, a $C_{3-6}$ cycloalkyl, a lower alkenyl, a heterocyclic group having N, O or S atom or camphor-10-yl; $R^3$ is hydrogen, a substituted or unsubstituted lower alkyl or a lower alkenyl; or $R^1$ and $R^3$ are bonded at terminal ends thereof to form a lower alkylene; and Z is a group represented by the formula:

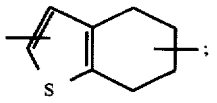

and $R^2$ is hydrogen, a substituted or unsubstituted lower alkyl, an aryl or a lower alkenyl; and —A—B— is an ethylene or vinylene each of which may be substituted by 1 or 2 groups selected from the group consisting of a lower alkyl and phenyl group, or a pharmaceutically acceptable salt thereof, and processes for preparing the same.

9 Claims, No Drawings

PYRIDAZINONE DERIVATIVES AND PROCESSES FOR PREPARING THE SAME

This application claims priority to application Ser. No. 08/430,249, filed on Apr. 28, 1994, now abandoned, which is a continuation of application Ser. No. 08/083,489, filed on Jun. 30, 1993, now abandoned, the entire contents of which are hereby incorporated by reference.

BACKGROUND OF THE INVENTION

This invention relates to novel pyridazinone derivatives having actions of protecting from endotoxin shock and actions of curing nephritis, and processes for preparing the same.

In Japanese Provisional Patent Publication No. 23853/1988, it has been disclosed that benzenesulfonamidindanyl compounds such as 6-(2-benzenesulfonamid-indan-5-yl)-4,5-dihydro-pyridazin-3(2H)-one exhibit antithrombotic actions.

Further, in Japanese Provisional Patent Publication No. 223277/1991, it has been disclosed that benzothiophene derivatives such as ethyl 4-[4-(4-chlorobenzenesulfonamidemethyl)-4,5,6,7-tetrahydrobenzo[b]thiophen-2-yl]-4-oxo-butanoate exhibit platelet aggregation inhibiting action.

On the other hand, as an agent for curing endotoxin shock which occurs in a patient seriously infected with gram-negative bacteria, there have been conventionally used steroid hormones, aprotinin (a protease inhibitor) and dobutamine (a cardiac).

Further, as an agent for curing nephritis, there have been conventionally used prednisolon, cyclophosphamide, dipyridamole, dilazep and heparin.

SUMMARY OF THE INVENTION

An object of the present invention is to provide novel compounds having excellent actions of protecting from endotoxin in shock and excellent actions of curing nephritis, and processes for preparing the same.

The pyridazinone derivative according to the present invention is represented by the formula (I):

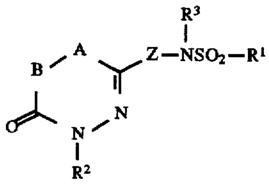

(I)

wherein (1) $R^1$ represents a substituted or unsubstituted alkyl group having 1 to 10 carbon atoms, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; $R^3$ represents hydrogen atom, a substituted or unsubstituted lower alkyl group or a lower alkenyl group; or $R^1$ and $R^3$ are bonded at terminal ends thereof to form a lower alkylene group; and Z represents a group represented by the formula:

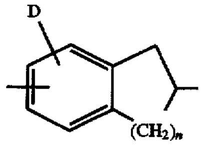

where n represents 1 or 2; and D represents hydrogen atom or a halogen atom; or (2) $R^1$ represents a substituted or unsubstituted alkyl group having 1 to 10 carbon atoms, a substituted or unsubstituted phenyl group, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; $R^3$ represents hydrogen atom, a substituted or unsubstituted lower alkyl group or a lower alkenyl group; or $R^1$ and $R^3$ are bonded at terminal ends thereof to form a lower alkylene group; and Z represents a group represented by the formula:

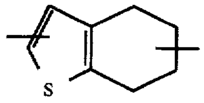
;

and $R^2$ represents hydrogen atom, a substituted or unsubstituted lower alkyl group, an aryl group or a lower alkenyl group; and —A—B— represents an ethylene group or vinylene group each of which may be substituted by 1 or 2 groups selected from the group consisting of a lower alkyl group and phenyl group.

The pyridazinone derivative of the present invention is specifically represented by the formula (I-a):

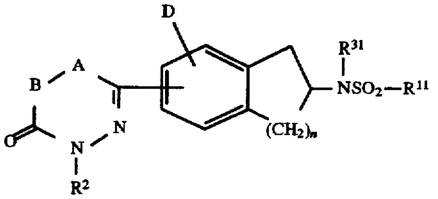

(I-a)

wherein $R^{11}$ represents a substituted or unsubstituted alkyl group having 1 to 10 carbon atoms, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; $R^{31}$ represents hydrogen atom, a substituted or unsubstituted lower alkyl group or a lower alkenyl group; or $R^{11}$ and $R^{31}$ are bonded at terminal ends thereof to form a lower alkylene group; and $R^2$, —A—B—, n and D have the same meanings as defined above, or the formula (I-b):

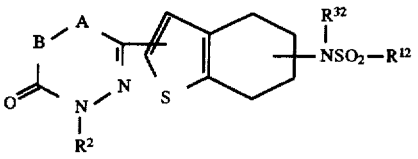

(I-b)

wherein $R^{12}$ represents a substituted or unsubstituted alkyl group having 1 to 10 carbon atoms, a substituted or unsubstituted phenyl group, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; $R^{32}$ represents hydrogen atom, a substituted or unsubstituted lower alkyl group or a lower alkenyl group; or $R^{12}$ and $R^{32}$ are bonded at terminal ends thereof to form a lower alkylene group; and $R^2$ and —A—B— have the same meanings as defined above.

DESCRIPTION OF THE PREFERRED EMBODIMENTS

In the following, the present invention is explained in detail.

As a specific example of the desired compound (I-a), there may be mentioned a compound in which $R^{11}$ is an alkyl group having 1 to 10 carbon atoms which may be substituted by a group selected from the group consisting of a phenyl group which may be substituted by 1 to 2 halogen atoms, a lower alkylthio group, phenylamino group and a heterocyclic group having nitrogen atom or sulfur atom as a hetero atom; a cycloalkyl group having 3 to 6 carbon atoms; a lower alkenyl group; a heterocyclic group having nitrogen atom, oxygen atom or sulfur atom as a hetero atom which may have a substituent(s); or camphor-10-yl group;

$R^{31}$ is hydrogen atom; a lower alkyl group which may be substituted by a group selected from the group consisting of phenyl group and a heterocyclic group having nitrogen atom or sulfur atom as a hetero atom which may have a substituent(s); or a lower alkenyl group; or $R^{11}$ and $R^{31}$ are bonded at terminal ends thereof to form a lower alkylene group;

$R^2$ is hydrogen atom; a lower alkyl group which may be substituted by a group selected from the group consisting of a phenyl group which may be substituted by 1 to 3 halogen atoms or 1 to 3 lower alkoxy groups, carboxyl group, a heterocyclic group having nitrogen atom, oxygen atom or sulfur atom as a hetero atom which may have a substituent(s), cyano group, a di-lower alkylcarbamoyl group, a lower alkoxycarbonyl group and a di-lower alkyl-amino group; an aryl group; or a lower alkenyl group;

—A—B— is an ethylene group or vinylene group each of which may be substituted by 1 or 2 groups selected from the group consisting of a lower alkyl group and phenyl group;

n is 1 or 2; and

D is hydrogen atom or a halogen atom.

In the desired compound (I-a), when $R^{11}$ is an alkyl group having 1 to 10 carbon atoms which is substituted by a heterocyclic group having nitrogen atom or sulfur atom as a hetero atom, said group may include an alkyl group having 1 to 10 carbon atoms which is substituted by pyridyl group or thienyl group, and when $R^{11}$ is a heterocyclic group having nitrogen atom, oxygen atom or sulfur atom as a hetero atom which may have a substituent(s), said group may include a thienyl group which may be substituted by pyridyl group, pyridyl group, a di-lower alkylthiazolyl group, a di-lower alkylisoxazolyl group, quinolyl group and a di-lower alkylhalogenopyrazolyl group. When $R^2$ is a lower alkyl group which is substituted by a heterocyclic group having nitrogen atom, oxygen atom or sulfur atom as a hetero atom which may have a substituent(s), said group may include a lower alkyl group which is substituted by a piperazinyl group which may be substituted by a lower alkoxycarbonyl group, imidazolyl group, thienyl group, pyridyl group, tetrazolyl group or morpholino group, and when $R^2$ is an aryl group, said group may include a phenyl group. When $R^{31}$ is a lower alkyl group which is substituted by a heterocyclic group having nitrogen atom or sulfur atom as a hetero atom which may have a substituent(s), said group may include a lower alkyl group substituted by a piperazinyl group which may be substituted by phenyl group, thienyl group or pyridyl group. When D is a halogen atom, said atom may include chlorine atom.

As another example of the desired compound (I-a), there may be mentioned a compound in which $R^{11}$ is an alkyl group having 1 to 10 carbon atoms, a cycloalkyl group having 3 to 6 carbon atoms, a phenylamino lower alkyl group or camphor-10-yl group; $R^2$ is a hydrogen atom, a lower alkyl group, a phenyl group or phenyl lower alkyl group; $R^{31}$ is a hydrogen atom; —A—B— is an ethylene group or a vinylene group each of which may be substituted by 1 or 2 groups selected from the group consisting of a lower alkyl group and a phenyl group; n is 1; and D is a hydrogen atom.

As a preferred compound, there may be mentioned a compound represented by the formula (I-a) wherein D is a hydrogen atom.

As a pharmaceutically preferred compound, there may be mentioned a compound represented by the formula (I-a) in which $R^{11}$ is an alkyl group having 1 to 10 carbon atoms which may be substituted by a group selected from the group consisting of a phenyl group, a thienyl group and a pyridyl group, a cycloalkyl group having 3 to 6 carbon atoms, a lower alkenyl group or camphor-10-yl group; $R^{31}$ is hydrogen atom, a lower alkyl group or a lower alkenyl group; or $R^{11}$ and $R^{31}$ are bonded at terminal ends thereof to form a lower alkylene group; $R^2$ is a hydrogen atom, a lower alkyl group which may be substituted by a group selected from the group consisting of a cyano group, a tetrazolyl group, a carboxyl group and a di-lower alkylcarbamoyl group, or a lower alkenyl group; —A—B— is ethylene group or vinylene group, n is 1 or 2; and D is hydrogen atom.

As a pharmaceutically more preferred compound, there may be mentioned a compound represented by the formula (I-a) in which $R^{11}$ is an alkyl group having 1 to 5 carbon atoms, benzyl group, cyclohexyl group, a lower alkenyl group or camphor-10-yl group, $R^2$ is hydrogen atom, a lower alkyl group which may be substituted by a group selected from the group consisting of a cyano group, tetrazolyl group, a carboxyl group and a di-lower alkyl carbamoyl group, or a lower alkenyl group, $R^{31}$ is hydrogen atom, a lower alkyl group or a lower alkenyl group, —A—B— is ethylene group or vinylene group, n is 1 or 2, and D is hydrogen atom, particularly a compound in which $R^{11}$ is an alkyl group having 1 to 5 carbon atoms or a lower alkenyl group, $R^2$ is hydrogen atom, a carboxyl lower alkyl group, a tetrazolyl lower alkyl group or a lower alkyl group, $R^{31}$ is hydrogen atom or a lower alkyl group, —A—B— is an ethylene group or a vinylene group, n is 1 or 2, and D is hydrogen atom.

In the desired compound (I) of the present invention, two kinds of optical isomers based on an asymmetric carbon atom exist. Both of these optical isomers and a mixture thereof are included in the present invention.

The desired compound (I) of the present invention can be formed into a pharmaceutically acceptable salt thereof. As the pharmaceutically acceptable salt, there may be mentioned, for example, inorganic acid salts such as hydrochloride, sulfate and hydrobromide, and organic acid salts such as fumarate, oxalate and maleate.

The desired compound (I) of the present invention can be administered either orally or parenterally, and it can be used as a medical preparation by mixing it with an excipient suitable for oral or parenteral administration. The medical preparation may be a solid preparation such as a tablet, a capsule and a powder, or a liquid preparation such as a solution, a suspension and an emulsion. Further, when the desired compound (I) is administered parenterally, it can be used in the form of an injection.

The dose varies depending on age, weight and state of a patient and disease conditions of a patient, but, in general, the dose per day is preferably 1 to 200 mg/kg, particularly 10 to 100 mg/kg in the case of oral administration, and it is preferably 0.1 to 30 mg/kg, particularly 1 to 20 mg/kg in the case of parenteral administration.

According to the present invention, the desired compound (I) or a pharmaceutically acceptable salt thereof can be prepared by reacting a compound represented by the formula (II):

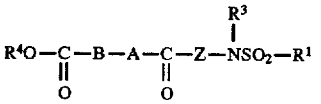

(II)

wherein $R^4$ represents hydrogen atom or a lower alkyl group; and $R^1$, $R^3$, Z and —A—B— have the same meanings as defined above, or a salt thereof, with a compound represented by the formula (III):

$R^2NH—NH_2$ (III)

wherein $R^2$ has the same meaning as defined above, and, if necessary, converting the resulting compound into a pharmaceutically acceptable salt thereof.

Among the desired compounds (I), a pyridazinone derivative represented by the formula (I-c):

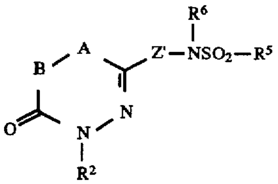

(I-c)

wherein (1) $R^5$ represents a substituted or unsubstituted alkyl group having 1 to 10 carbon atoms, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group, and Z' is a group represented by the formula:

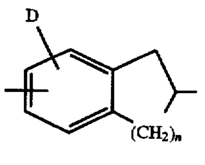

where n and D have the same meanings as defined above; or (2) $R^5$ represents a substituted or unsubstituted alkyl group having 1 to 10 carbon atoms, a substituted or unsubstituted phenyl group, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group, and Z' is a group represented by the formula:

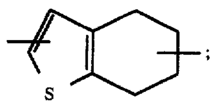

;

$R^6$ represents hydrogen atom, a substituted or unsubstituted lower alkyl group or a lower alkenyl group; and $R^2$ and —A—B— have the same meanings as defined above, or a pharmaceutically acceptable salt thereof, can be prepared by reacting a compound represented by the formula (IV):

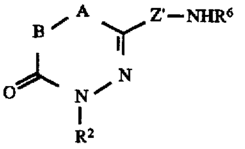

(IV)

wherein $R^2$, $R^6$, Z' and —A—B— have the same meanings as defined above, or a salt thereof, with a compound represented by the formula (V):

$R^5—SO_2—X^1$ (V)

wherein $X^1$ represents a reactive residue; and $R^5$ has the same meaning as defined above.

and, if necessary, converting the resulting compound into a pharmaceutically acceptable salt thereof.

Among the desired compounds (I), a pyridazinone derivative represented by the formula (I-e):

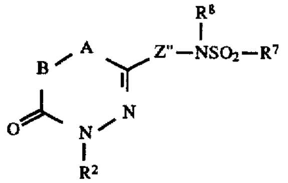

(I-e)

wherein (1) $R^7$ represents a substituted or unsubstituted alkyl group having 1 to 10 carbon atoms, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; and Z" represents a group represented by the formula:

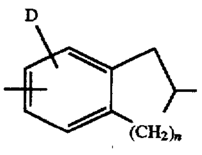

where D and n have the same meanings as defined above; or (2) $R^7$ represents a substituted or unsubstituted alkyl group having 1 to 10 carbon atoms, a substituted or unsubstituted phenyl group, a cycloalkyl group having 3 to 6 carbon atoms, a lower alkenyl group, a heterocyclic group having nitrogen atom, oxygen atom or sulfur atom as a hetero atom which may have a substituent(s) or camphor-10-yl group; and Z" represents a group represented by the formula:

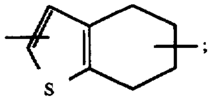

$R^8$ represents a substituted or unsubstituted lower alkyl group or a lower alkenyl group; and $R^2$ and —A—B— have the same meanings as defined above, or a pharmaceutically acceptable salt thereof, can be prepared by reacting a compound represented by the formula (I-d):

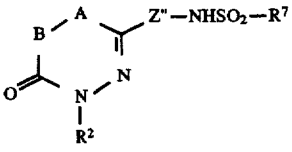
(I-d)

wherein $R^2$, $R^7$, Z" and —A—B— have the same meanings as defined above, or a salt thereof, with a compound represented by the formula (VI):

$$R^8—X^2 \qquad (VI)$$

wherein $X^2$ represents a reactive residue and $R^8$ has the same meaning as defined above, and, if necessary, converting the resulting compound into a pharmaceutically acceptable salt thereof.

Among the desired compounds (I), a pyridazinone derivative represented by the formula (I-g):

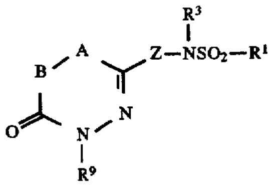
(I-g)

wherein $R^9$ represents a substituted or unsubstituted lower alkyl group, an aryl group or a lower alkenyl group; and $R^1$, $R^3$, Z and —A—B— have the same meanings as defined above, or a pharmaceutically acceptable salt thereof, can be prepared by reacting a compound represented by the formula (I-f):

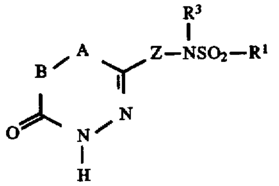
(I-f)

wherein $R^1$, $R^3$, Z and —A—B— have the same meanings as defined above, or a salt thereof, with a compound represented by the formula (VII):

$$R^9—X^3 \qquad (VII)$$

wherein $X^3$ represents a reactive residue; and $R^9$ have the same meaning as defined above, and, if necessary, converting the resulting compound into a pharmaceutically acceptable salt thereof.

Among the desired compounds (I), a pyridazinone derivative represented by the formula (I-i):

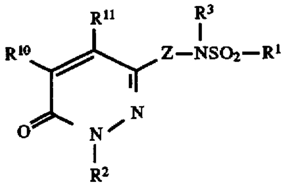
(I-i)

wherein $R^{10}$ and $R^{11}$ are the same or different and represent hydrogen atom, a lower alkyl group or a phenyl group, and $R^1$, $R^2$, $R^3$ and Z have the same meanings as defined above, or a pharmaceutically acceptable salt thereof, can be prepared by oxidizing a compound represented by the formula (I-h):

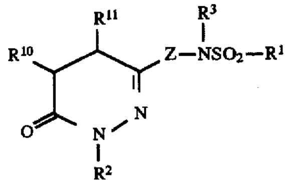
(I-h)

wherein $R^1$, $R^2$, $R^3$, $R^{10}$, $R^{11}$ and Z have the same meanings as defined above, or a salt thereof, and, if necessary, converting the resulting compound into a pharmaceutically acceptable salt thereof.

In the above preparation process of the present invention, the reaction of the compound (II) and the hydrazine compound (III) can be carried out suitably in the presence or absence of a suitable solvent.

The solvent may be any inactive solvent which does not exert bad influence on the reaction, and may include, for example, a lower alcohol, a lower aliphatic acid such as acetic acid and propionic acid, an aromatic hydrocarbon such as toluene and xylene, and an ether such as tetrahydrofuran and dioxane.

The hydrazine compound (III) may be a hydrate.

The reaction can be carried out at a wide range of temperature from room temperature to a boiling point of a reaction mixture, for example, preferably 10° C. to 200° C., particularly 20° C. to 150° C.

The condensation reaction of the compound (IV) and the compound (V) can be carried out suitably in a suitable solvent in the presence or absence of an acid acceptor, respectively.

As the reactive residue ($X^1$) of the compound (V), a group which splits off nucleophilically, for example, a halogen atom or an alkoxy group may be suitably used, or when the compound (V) is a symmetric sulfonic anhydride, a lower alkylsulfonyloxy group, benzenesulfonyloxy group or a lower alkyl group-substituted benzenesulfonyloxy group may be suitably used.

As the acid acceptor, there may be used suitably, for example, organic bases such as a tri-lower alkylamine, an N-lower alkylmorpholine, pyridine and 2,6-lutidine, and inorganic bases such as an alkali metal hydroxide, an alkali metal hydrogen carbonate, an alkali metal carbonate and an alkali metal hydride.

The solvent may be any innert solvent which does not exert bad influence on the reaction, and may include, for example, halogen type solvents such as chloroform, dichloromethane and dichloroethane; aromatic hydrocarbons such as toluene and xylene; ethers such as tetrahydrofuran and dioxane; ketone type solvents such as acetone and methyl ethyl ketone; esters such as ethyl acetate; acetonitrile; pyridine; 2,6-lutidine; dimethylformamide; dimethyl-sulfoxide; 1,3-dimethyl-2-imidazolidinone; and a combination of these solvents and water.

The condensation reaction can be carried out at a wide range of temperature from −78° C. to a boiling point of a reaction mixture, for example, preferably −0° C. to 150° C., particularly −10° C. to 80° C.

The condensation reactions of the compound (I-d) and the compound (VI), and the compound (I-f) and the compound (VII) can be carried out suitably in a suitable solvent in the presence of a base, respectively.

As the reactive residues ($X^2$ and $X^3$) of the compounds (VI) and (VII), a group which splits off nucleophilically, for example, a halogen atom, an alkoxy group, a lower alkylsulfonyloxy group, a benzenesulfonyloxy group, a lower alkyl-substituted benzenesulfonyloxy group and a trifluoromethanesulfonyloxy group may be suitably used.

As the base, there may be used suitably, for example, lower alkyl metal such as n-butyl lithium, alkali metal alkoxide, alkali metal hydroxide, alkali metal carbonate and alkali metal hydride.

The solvent may be any innert solvent which does not exert bad influence on the reaction, and may include, for example, ethers such as dimethoxyethane, tetrahydrofuran and dioxane; alcohols such as methanol, ethanol, 2-methoxyethanol, propanol and butanol; ketones such as acetone and methyl ethyl ketone; esters such as ethyl acetate; amide type solvents such as dimethylformamide, dimethylacetamide and 1,3-dimethyl-2-imidazolidinone; acetonitrile; and dimethylsulfoxide.

The condensation reaction can be carried out under cooling or with heating, particularly 0° C. to 150° C.

The oxidation of the compound (I-h) can be carried out according to a conventional method, and it can be carried out preferably by, for example, treating the compound (I-h) with sodium 3-nitrobenzenesulfonate in a suitable solvent under basic conditions; subjecting it to oxidation by using dimethylsulfoxide under acidic conditions; or treating it with hydrogen bromide-acetic acid or the like.

As the solvent, there may be used suitably water, acetic acid, trifluoroacetic acid, methanesulfonic acid and an acetic acid solution of hydrogen bromide.

In the reactions of the present invention, by using an optical isomer as the starting compound (II), (IV), (I-d), (I-f) or (I-h), a corresponding optically active desired compound (I), (I-C), (I-e), (I-g) or (I-i) can be obtained, respectively, without racemization.

The starting compound (II) can be prepared by, for example, reacting a compound represented by the formula (X):

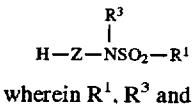

(X)

wherein $R^1$, $R^3$ and Z have the same meanings as defined above, which can be obtained by reacting a compound represented by the formula (VIII):

$$H—Z'—NHR^6 \quad (VIII)$$

wherein $R^6$ and Z' have the same meanings as defined above, with the sulfone compound (V) or a compound represented by the formula (IX):

$$X^5—SO_2—E—X^4 \quad (IX)$$

wherein E represents a lower alkylene group; and $X^4$ and $X^5$ each represent a reactive residue, and, if necessary, further carrying out cyclization in the molecule, with a compound represented by the formula (XI):

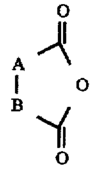

(XI)

wherein —A—B— has the same meaning as defined above, or a compound represented by the formula (XII):

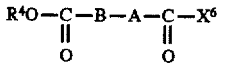

(XII)

wherein $X^6$ represents a reactive residue; and $R^4$ and —A—B— have the same meanings as defined above.

The starting compound (IV) can be prepared by, for example, reacting a compound represented by the formula (XIII):

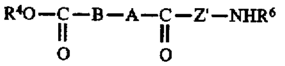

(XIII)

wherein $R^4$, $R^6$, Z' and —A—B— have the same meanings as defined above, with the hydrazine compound (III), and when —A—B— is ethylene group, further oxidizing the reaction product to convert said ethylene group into vinylene group, if desired.

The starting compound (XIII) of the above reaction can be prepared by, for example, a method in which, if necessary, after an amino group of the compound (VIII) is protected, said compound is reacted with the compound (XI) or (XII), and then the protective group is removed, or a method described below in Examples described below.

In the present specification, the lower alkyl group, lower alkoxy group and lower alkylene group include those having 1 to 6 carbon atoms, and the lower alkenyl group includes those having 2 to 7 carbon atoms.

EXAMPLES

The present invention is described in detail by referring to Examples.

Test example 1

(Action of protecting mouse from death induced by endotoxin)

To ddy strain male mice which had fasted for about 24 hours, a test sample, 2-[4,5-dihydropyridazin-3(2H)-on-6-yl]-5-(n-butylsulfonylamino)-4,5,6,7-tetrahydrobenzo[b]thiophene dissolved or suspended in a 0.25% sodium carboxymethyl cellulose (CMC) aqueous solution was orally administered (100 mg/kg). After 30 minutes, 100 mg/10 ml/kg of endotoxin (lipopolysaccharide) derived from *Escherichia coli* dissolved in physiological saline was administered intraperitoneally. When the survival rate of the control group to which the CMC aqueous solution had been orally administered became 20% (about 20 hours after administration of endotoxin), the survival rate of the group to which the test sample had been administered was determined. As a result, the survival rate of the group to which the test sample had been administered was 90%.

Test example 2

(Action of protecting mouse from death induced by endotoxin)

To ddy strain male mice which had fasted for about 24 hours, a test sample, 2-methylsulfonylamino-5-[4,5-dihydropyridazin-3(2H)-on-6-yl]indane dissolved or suspended in a 0.25% sodium carboxymethyl cellulose (CMC) aqueous solution was orally administered (100 mg/kg). After 30 minutes, 100 mg/10 ml/kg of endotoxin (lipopolysaccharide) derived from *Escherichia coli* dissolved in physiological saline was administered intraperitoneally. When the survival rate of the control group to which the CMC aqueous solution had been orally administered became 20% (about 20 hours after administration of endotoxin), the survival rate of the group to which the test sample had been administered was determined. As a result, the survival rate of the group to which the test sample had been administered was 100%.

Test example 3

(Action of curing nephritis)

To male WKY rats (8 weeks old, 6 rats per group), 2.5 ml/kg of a rabbit anti-glomerular basement membrane serum diluted by 50 times with physiological saline was administered intravenously to induce nephritis. A test sample, 2-propylsulfonylamino-5-[pyridazin-3(2H)-on-6-yl]indane suspended in purified water by using Tween 80 (trade name, produced by Nacalai Tesque Co.) was orally administered in a dose of 30 mg/kg/10 ml twice a day for 8 days. Eight days after induction of nephritis, urine was collected for 24 hours. By measuring urine volumes and measuring concentrations of protein in urine by the sulfosalicylic acid method, amounts of protein excreted in urine were calculated. The protein excretion of the group which had been administered the test sample was decreased to 50 to 55% protein excretion of the control group.

Example 1

1.4 g of potassium carbonate dissolved in 20 ml of water was added to 1.15 g of 2-amino-5-[4,5-dihydropyridazin-3(2H)-on-6-yl]indane dissolved in 40 ml of ethyl acetate and 20 ml of tetrahydrofuran. Then, 0.57 g of methanesulfonyl chloride was added thereto and the mixture was stirred for 2 hours. After the organic layer was collected by separation and dried, the solvent was removed. The resulting crystals were recrystallized from tetrahydrofuran-isopropyl ether to obtain 1.08 g of 2-methylsulfonylamino-5-[4,5-dihydropyridazin-3(2H)-on-6-yl]indane.

m.p.: 218° to 220° C.

Example 2

6.3 g of n-butanesulfonyl chloride was added under ice cooling to 5.61 g of 2-amino-5-[4,5-dihydropyridazin-3(2H)-on-6-yl]indane and 4.1 g of triethyl amine suspended in 50 ml of chloroform, and the mixture was stirred for 1 hour. Diluted hydrochloric acid was added to the reaction mixture, the chloroform layer was collected by separation, washed and dried, and then the solvent was removed. The resulting crystals were recrystallized from tetrahydrofuran-isopropyl ether to obtain 6.40 g of 2-n-butylsulfonylamino-5-[4,5-dihydropyridazin-3(2H)-on-6-yl]indane.

m.p.: 183° to 185° C.

Examples 3 to 28

By treating the corresponding starting compounds in the same manner as in Example 2, compounds shown in the following Table 1 were obtained.

TABLE 1

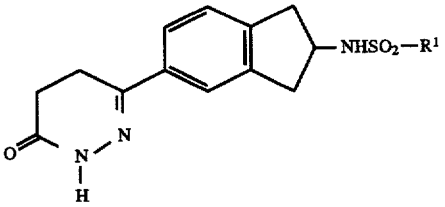

| Example No. | $R^1$ | Physical properties |
|---|---|---|
| 3 | $-C_2H_5$ | m.p. 177–178° C. |
| 4 | $-n-C_3H_7$ | m.p. 178–179° C. |
| 5 | $-CH_2CH(CH_3)_2$ | m.p. 193.5–194.5° C. |
| 6 | $-n-C_5H_{11}$ | m.p. 175.5–176.5° C. |
| 7 | $-n-C_6H_{13}$ | m.p. 173–174° C. |
| 8 | $-n-C_7H_{15}$ | m.p. 174–175° C. |
| 9 | $-n-C_8H_{17}$ | m.p. 193–195° C. |
| 10 | 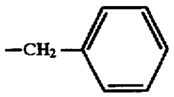 | m.p. 211–213° C. |
| 11 | 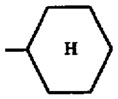 | m.p. 158–160° C. |
| 12 | camphor-10-yl | m.p. 205–208° C. |
| 13 | 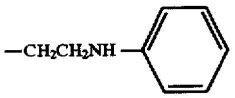 | m.p. 163–166° C. |
| 14 | $-CH(CH_3)_2$ | m.p. 160–162° C. |
| 15 | 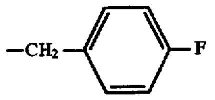 | m.p. 219–221° C. (dec) |
| 16 | 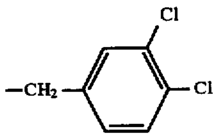 | m.p. 249–250° C. (dec) |
| 17 | 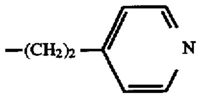 | m.p. 147–149° C. |
| 18 | 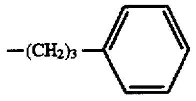 | m.p. 160–162° C. |
| 19 | 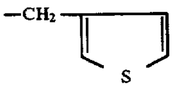 | m.p. 227–229° C. |
| 20 | 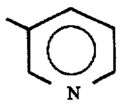 | m.p. 207–208° C. |

TABLE 1-continued

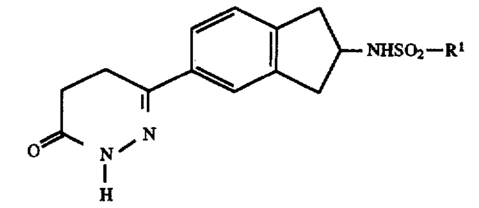

| Example No. | $R^1$ | Physical properties |
|---|---|---|
| 21 | 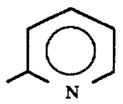 | m.p. 210–211° C. |
| 22 | 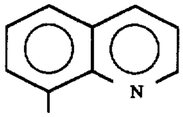 | m.p. 228–230° C. |
| 23 | 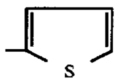 | m.p. 194–196° C. |
| 24 | 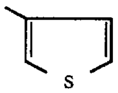 | m.p. 170–172° C. |
| 25 | 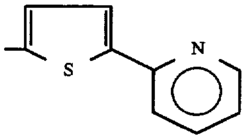 | m.p. 212–214° C. |
| 26 | 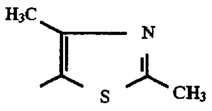 | m.p. 209–210° C. |
| 27 | 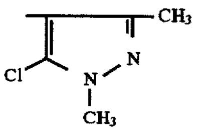 | m.p. 227–228° C. |
| 28 | 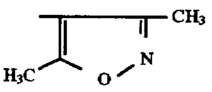 | m.p. 229–231° C. |

Example 29

(1) In 1,400 ml of ethanol was dissolved 8.41 g of 2-amino-5-[4,5-dihydropyridazin-3(2H)-on-6-yl]indane, and 8.52 g of (+)-camphorsulfonic acid was added thereto. The resulting salts were recrystallized from ethanol several times to obtain 5.20 g of optically active 2-amino-5-[4,5-dihydropyridazin-3(2H)-on-6-yl]indane. (+)-camphorsulfonate.

m.p.: 256° to 257° C. (decomposed)

$[\alpha]_D$: −13.4° (c=1.00, $H_2O$).

(2) The product obtained was treated in the same manner as in Example 2 to obtain (+)-2-n-butylsulfonylamino-5-[4,5-dihydropyridazin-3(2H)-on-6-yl]indane.

m.p.: 173° to 174° C.

$[\alpha]_D$: +33.2° (c=1.00, dimethylformamide (DMF)).

Example 30

(1) All mother liquor of Example 29-(1) was recovered and neutralized with a potassium carbonate aqueous solution, and ethanol was removed. The residue was extracted with ethyl acetate, and ethyl acetate was removed. In 1,000 ml of ethanol was dissolved 5.23 g of the residue, and 5.29 g of (−)-camphorsulfonic acid was added thereto. The resulting salts were recrystallized from ethanol several times to obtain 4.99 g of optically active 2-amino-5-[4,5-dihydropyridazin-3(2H)-on-6-yl]indane. (−)-camphorsulfonate.

m.p.: 257° to 258° C. (decomposed) $[\alpha]_D$: +13.1° (c=100, $H_2O$). (2) The product obtained was treated in the same manner as in Example 2 to obtain (−)-2-n-butylsulfonylamino-5-[4,5-dihydropyridazin-3(2H)-on-6-yl]indane. m.p.: 173 to 174° C $[\alpha]_D$: −33.4° (c=1.00, DMF).

Example 30

(1) All mother liquor of Example 29-(1) was recovered and neutralized with a potassium carbonate aqueous solution, and ethanol was removed. The residue was extracted with ethyl acetate, and ethyl acetate was removed. In 1,000 ml of ethanol was dissolved 5.23 g of the residue and 5.29 g of (−)-camphorsulfonic acid was added thereto. The resulting salts were recrystallized from ethanol several times to obtain 4.99 g of optically active 2-amino-5-[4,5-dihydropyridazin-3(2H)-on-6yl]indane. (−)-camphorsulfonate.

m.p.: 257° to 258° C. (decomposed)

$[\alpha]_D$: +13.1° (c=1.00, $H_2O$).

(2) The product obtained was treated in the same manner as in Example 2 to obtain (−)-2n-butylsulfonylamino-5-[4,5-dihydropyridazin-3(2H)-on-6yl]indane.

m.: 173° to 174° C.

$[\alpha]_D$: −33.4° (c=1.00, DMF).

Example 31

(1) To 87.44 g of 2-aminoindane dissolved in 800 ml of methylene chloride was added 66.43 g of triethylamine, and 102.8 g of n-butylsulfonyl chloride was added dropwise thereto under ice cooling. The mixture was stirred at the same temperature for 1 hour. The reaction mixture was washed with diluted hydrochloric acid and dried, and then the solvent was removed. The resulting crystals were recrystallized from isopropyl ether to obtain 151.12 g of 2-n-butylsulfonylaminoindane.

m.p.: 60° to 62° C.

(2) To 29.22 g of the product obtained and 23.05 g of succinic anhydride suspended in 300 ml of dichloroethane was added 62.96 g of anhydrous aluminum chloride under ice cooling, and the mixture was stirred at room temperature for 1 hour. To the reaction mixture were added 200 ml of 10% hydrochloric acid under ice cooling and then 700 ml of ethyl acetate. After the organic layer was collected by separation, washed and dried, the solvent was removed. The resulting crystals were recrystallized from ethyl acetate to obtain 29.77 g of 2-n-butylsulfonylamino-5-(3-carboxypropionyl)indane.

m.p.: 138.5° to 139.5° C.

(3) In 200 ml of ethanol was dissolved 17.30 g of the product obtained, and 12.5 g of hydrazine monohydrate was added thereto. The mixture was refluxed under heating for 2.5 hours. The solvent was removed from the reaction mixture, and the residue was washed with water, dried and recrystallized from tetrahydrofuran-isopropyl ether to obtain 12.04 g of 2-n-butylsulfonylamino-5-[4,5-dihydropyridazin-3(2H)-on-6-yl]indane.

m.p.: 183° to 185 C.

Examples 32 to 34

By reacting 2-n-butylsulfonyl amino-5-(3-carboxypropionyl)-indane with substituted hydrazine in the same manner as in Example 31, compounds shown in the following Table 2 were obtained.

TABLE 2

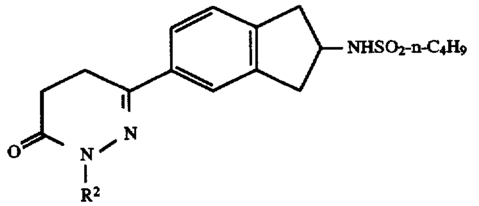

| Example No. | $R^2$ | Physical properties |
|---|---|---|
| 32 | 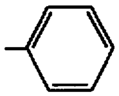 | m.p. 128.5–129.5° C. |
| 33 | 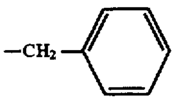 | m.p. 124–125° C. |
| 34 | $-CH_3$ | m.p. 119–122° C. |

Example 35

(1) To 200 ml of acetic acid were added 26.4 g of 2-amino-indane and 44.5 g of phthalic anhydride, and the mixture was refluxed under heating for 17 hours. The reaction mixture was poured into ice water, and crystals precipitated were collected by filtration, washed, dried and then recrystallized from ethyl acetate to obtain 45.04 g of 2-(1,3-isoindolinedion-2-yl)indane.

m.p.: 200° to 202° C.

(2) in 30 ml of carbon disulfide was suspended 1.60 g of anhydrous aluminum chloride, and to the suspension were added under ice cooling 580 mg of dimethyl succinic anhydride and then 790 mg of 2-(1,3-isoindolinedion-2-yl) indane. The mixture was stirred at 0° C. to room temperature for 3 hours and then refluxed under heating for 4 hours. The reaction mixture was poured into ice water, and hydrochloric acid was added thereto. The mixture was extracted with dichloromethane-tetrahydrofuran (3:1), the extract was dried, and then the solvent was removed. The resulting crystals were washed with ethyl acetate and dried to obtain 580 mg of 2-(1,3-isoindolinedion-2-yl)-5-(3-carboxy-3,3-dimethylpropionyl)indane.

m.p.: 238° to 240° C.

(3) In 300 ml of methanol was suspended 9.80 g of the product obtained, 5.06 g of hydrazine monohydrate was added thereto, and the mixture was refluxed under heating for 3 hours. After cooling, insolubles were removed, and the solvent was removed. Then, the residue was dissolved in chloroform, insolubles were removed, and the solvent was removed. The resulting crystals were recrystallized from chloroform-n-hexane to obtain 5.04 g of 2-amino-5-[4,4-dimethyl-4,5-dihydropyridazin-3(2H)-on-6-yl]indane.

m.p.: 175° to 177° C.

(4) To 1.29 g of the product obtained dissolved in 60 ml of dichloromethane-tetrahydrofuran (2:1) was added 1.38 g of potassium carbonate dissolved in 20 ml of water, and 1.12 g of methanesulfonyl chloride dissolved in 20 ml of dichloromethane was added dropwise thereto. The mixture was stirred at room temperature for 1 hour. After the organic layer was collected by separation and dried, the solvent was removed. The resulting crystals were recrystallized from tetrahydrofuran-isopropyl ether to obtain 1.46 g of 2-methyl sulfonylamino-5-[4,4-dimethyl-4,5-dihydropyridazin-3(2H) -on-6-yl]indane.

m.p.: 215° to 216° C.

Example 36

(1) To 8.00 g of anhydrous aluminum chloride suspended in 100 ml of dichloroethane was added dropwise 3.20 g of 2-methylpropanoyl chloride dissolved in 50 ml of dichloroethane under ice cooling. Then, to the mixture was added 5.27 g of 2-(1,3-isoindolinedion-2-yl)indane, and the mixture was stirred for 3 hours. The reaction mixture was poured into ice water containing hydrochloric acid, the organic layer was collected by separation, washed with water and dried, and then the solvent was removed. The resulting crystals were recrystallized from ethyl acetate-n-hexane to obtain 4.92 g of 2-(1,3-isoindolinedion-2-yl )-5-(2-methylpropionyl)indane.

m.p.: 138° to 140° C.

(2) Lithium bis(trimethylsilyl)amide prepared from 1.78 g of 1,1,1,3,3,3-hexamethylsilazane and n-butyl lithium (6.9 ml of 1.6M hexane solution), dissolved in 50 ml of tetrahydrofuran was cooled to −40° C., and 3.30 g of 2-(1,3-isoindolinedion-2-yl)-5-(2-methylpropionyl)indane dissolved in 50 ml of tetrahydrofuran was added dropwise thereto over 15 minutes. The mixture was stirred at 0° C. for 20 minutes and cooled to −30° C. To the mixture was added dropwise 1.68 g of methyl bromoacetate dissolved in 10 ml of tetrahydrofuran, and the mixture was stirred at room temperature for 2.5 hours. To the reaction mixture was added a saturated ammonium chloride solution, the mixture was extracted with ethyl acetate, the extract was dried, and then the solvent was removed. The residue was purified by silica gel column chromatography (eluted by n-hexane:ethyl acetate =4:1). The resulting crystals were recrystallized from ethyl acetate-n-hexane to obtain 2.06 g of 2-(1,3-isoindolinedion-2-yl)-5-(2,2-dimethyl-3-methoxycarbonyl-propionyl)indane.

m.p.: 115° to 117° C.

(3) To 5.55 g of the product obtained suspended in 100 ml of methanol was added 25 ml of a 1N potassium hydroxide aqueous solution, and the mixture was stirred at room temperature for 2 hours. Methanol was removed by distillation, and the residue was made acidic by adding 5% hydrochloric acid and extracted with ethyl acetate. After the organic layer was washed with water and dried, the solvent was removed to obtain 5.07 g of 2-(1,3-isoindolinedion-2-yl)-5-(2,2-dimethyl-3-carboxypropionyl)indane.

(4) To 5.07 g of the product obtained dissolved in 200 ml of isopropanol was added 3.4 g of hydrazine monohydrate, and the mixture was refluxed under heating overnight. In-solubles formed were removed, and the solvent was removed. The residue was washed with water and dried to obtain 3.01 g of 2-amino-5-[5,5-dimethyl-4,5-dihydropyridazin-3(2H)-on-6-yl]indane.

(5) To 3.01 g of the product obtained and 1.7 g of tri-ethylamine suspended in 100 ml of methylene chloride was added 2.4 g of butylsulfonyl chloride under cooling, and the mixture was stirred at the same temperature for 2 hours and then at room temperature for 2 hours. The reaction mixture was poured into ice water, the organic layer was collected by separation, washed with water and dried, and the solvent was removed. The residue was purified by silica gel column chromatography (eluted by chloroform: ethyl acetate=3:1). The resulting crystals were recrystallized from chloroform-isopropyl ether to obtain 2.33 g of 2-n-butylsulfonylamino-5-[5,5-dimethyl-4,5-dihydropyridazin-3(2H)-on-6-yl]indane.

m.p.: 159° to 161° C.

Example 37

(1) 0.70 g of phenylacetic acid chloride dissolved in 5 ml of dichloroethane was added under ice cooling to 1.00 g of 2-(1,3-isoindolinedion-2-yl)indane and 1.27 g of anhydrous aluminum chloride suspended in 15 ml of dichloroethane, and the mixture was stirred at the same temperature for 2 hours and then at room temperature for 1 hour. The reaction mixture was poured into ice water and extracted with chloroform. After the organic layer was washed with water and dried, the solvent was removed. The resulting crystals were recrystallized from ethyl acetate to obtain 1.05 g of 2-(1,3-isoindolinedion-2-yl)-5-(2-phenylacetyl)indane.

m.p.: 162° to 164° C.

(2) To 1.35 g of 60% sodium hydride suspended in 100 m of dimethylformamide was added dropwise 11.64 g of the compound obtained above dissolved in 50 ml of dimethylformamide under ice cooling and stirring. After 10 minutes, to the mixture was added dropwise 5.16 g of methyl bromoacetate dissolved in 50 ml of dimethylformamide, and the mixture was stirred for 1.5 hours. The reaction mixture was poured into ice water and extracted with ethyl acetate. After the organic layer was washed with water and dried, the solvent was removed. The resulting crystals were recrystallized from ethyl acetate-n-hexane to obtain 11.14 g of 2-(1,3-isoindolinedion-2-yl )-5-(2-phenyl-3-methoxycarbonyl propionyl)indane.

m.p.: 163° to 165° C.

(3) To 4.00 g of the product obtained dissolved in 40 m of ethanol was added 2.21 g of hydrazine monohydrate, and the mixture was refluxed under heating for 20 minutes. The solvent was removed, 80 ml of chloroform was added to the residue, and insolubles were removed. After the organic layer was washed with water and dried, the solvent was removed to obtain 2.90 g of 2-amino-5-(2-phenyl-3-methoxycarbonylpropionyl)indane as an oily product.

$IR^{neat}$ $\nu_{max}$ ($cm^{-1}$): 3370, 1735, 1675

Mass (m/z): 323 ($M^+$).

(4) To 2.90 g of the product obtained and 1.78 g of triethylamine dissolved in 30 ml of chloroform was added 2.07 g of butylsulfonyl chloride under ice cooling, and the mixture was stirred at room temperature for 30 minutes. The reaction mixture was poured into ice water and extracted with ethyl acetate. After the organic layer was washed and dried, the solvent was removed. The residue was purified by silica gel column chromatography (eluted by hexane:ethyl acetate=2:1) to obtain 2.66 g of 2-n-butylsulfonylamino-5-(2-phenyl-3-methoxycarbonylpropionyl)indane as an oily product.

$IR^{neat}$ $\nu_{max}$ ($cm^{-1}$): 3280, 1735, 1675

Mass (m/z): 443 ($M^+$).

(5) To 2.66 g of the product obtained dissolved in 30 ml of methanol was added 15 ml of a IN sodium hydroxide aqueous solution, and the mixture was refluxed under heating for 30 minutes. Methanol was removed from the reaction mixture, and the residue was made acidic by adding 5% hydrochloric acid and then extracted with ethyl acetate. After the organic layer was washed and dried, the solvent was removed to obtain 2.57 g of 2-n-butylsulfonylamino-5-(2-phenyl-3-carboxypropionyl) indane.

(6) To 2.57 g of the product obtained dissolved in 30 ml of ethanol was added 1.46 g of hydrazine monohydrate, and the mixture was refluxed under heating for 3.5 hours. The solvent was removed from the reaction mixture, and the resulting crystals were recrystallized from methanol to obtain 1.65 g of 2-n-butylsulfonyl amino-5-[5-phenyl-4,5-dihydropyridazin-3(2H)-on-6-yl]indane.

m.p.: 158° to 160° C.

Example 38

(1) 2-n-Butylsulfonylaminoindane and acetyl chloride were treated in the same manner as in Example 31-(2) to obtain 2-n-butylsulfonylamino-5-acetylindane.

m.p.: 90° to 92° C.

(2) To 1.45 g of sodium hydroxide dissolved in 13 ml of water and 100 ml of ethanol were added 4.00 g of 2-n-butylsulfonylamino-5-acetylindane and 1.92 g of benzaldehyde under ice cooling, and the mixture was stirred at room temperature for 16 hours. Ethanol was removed from the reaction mixture, and the residue was neutralized with 10% hydrochloric acid and extracted with chloroform. After the organic layer was washed with water and dried, the solvent was removed. The resulting crystals were recrystallized from isopropanol to obtain 4.47 g of 2-n-butyl sulfonylamino-5-(3-phenylacryloyl)indane.

m.p.: 119° to 120° C.

(3) TO 7.70 g of the product obtained and 17.0 g of acetone cyanhydrin dissolved in 500 ml of methanol was added 1.05 g of sodium carbonate dissolved in 10 ml of water, and the mixture was refluxed under heating overnight. Methanol was removed from the reaction mixture, and the residue was extracted with ethyl acetate. After the organic layer was washed with water and dried, the solvent was removed. The residue was purified by silica gel column chromatography (eluted by n-hexane:ethyl acetate=2:1) to 10 obtain 6.56 g of 2-n-butylsulfonylamino-5-(3-cyano-3-phenylpropionyl) indane as an oily product.

$IR^{neat}$ $\nu_{max}$ ($cm^{-1}$): 3270, 2320, 1680

Mass (m/z): 410 ($M^+$).

(4) To 6.56 g of the product obtained dissolved in 300 m of dioxane was added 300 ml of 10N hydrochloric acid, and the mixture was refluxed under heating for 5 hours. To the reaction mixture was added 300 ml of water, and the mixture was extracted with ethyl acetate. After the organic layer was washed with water and dried, the solvent was removed to obtain 6.5 g of 2-n-butyl sulfonylamino-5-(3-carboxy-3-phenylpropionyl) indane.

(5) To 6.5 g of the product obtained dissolved in 120 ml of ethanol was added 3.50 g of hydrazine monohydrate, and the mixture was refluxed under heating for 4 hours. After cooling, crystals precipitated were collected by filtration to obtain 4.71 g of 2-n-butylsulfonylamino-5-[4-phenyl-4,5-dihydropyridazin-3(2H)-on-6-yl]indane.

m.p.: 216° to 217° C.

Example 39

(1) In 100 ml of tetrahydrofuran was suspended 5.7 g of lithium aluminum hydride, and to the suspension was added dropwise 18.9 g of 2-propionyl aminoindane dissolved in 150 ml of tetrahydrofuran. The mixture was refluxed under heating for 2 hours. After cooling, excessive lithium aluminum hydride was treated with a saturated ammonium chloride aqueous solution, and insolubles were removed by filtration. The filtrate was condensed, and chloroform was added to the residue. After the mixture was washed with water and dried, the solvent was removed to obtain 17.5 g of 2-propylaminoindane.

In 200 ml of tetrahydrofuran were dissolved 17.5 g of the product obtained and 12.12 g of triethylamine, and to the solution was added dropwise 17.8 g of methyl chlorocarbonate under cooling. The mixture was stirred at room temperature for 2 hours, tetrahydrofuran was removed, and ethyl acetate was added to the residue. After the mixture was washed with water and dried, the solvent was removed to obtain 21.6 g of 2-(N-methoxycarbonyl-N-propyl) aminoindane.

$IR^{neat}$ $\nu_{max}$ ($cm^{-1}$): 1660

Mass (m/z): 233 ($M^+$).

(2) To 21.6 g of the product obtained and methylsuccinyl chloride (prepared from 24.68 g of methyl hydrogen succinate and 23.75 g of oxalyl chloride) dissolved in 300 m of dichloromethane was added 59.85 g of anhydrous aluminum chloride under ice cooling, and the mixture was stirred at room temperature for 2 hours. The reaction mixture was poured into ice water, the organic layer was collected by separation, washed with water and dried, and then the solvent vent was removed to obtain 33.72 g of 2-(N-methoxycarbonyl-N-propyl)amino-5-(3-methoxycarbonylpropionyl)indane.

To 33.72 g of the product obtained dissolved in xylene were added 12.75 g of hydrazine monohydrate and 24 ml of acetic acid, and the mixture was refluxed under heating for 4 hours. The reaction mixture was poured into ice water and extracted with ethyl acetate, the extract was washed with water and dried, and then the solvent was removed. The residue was solidified in a mixed solution of diisopropyl ether and hexane to obtain 28.96 g of 2-(N-methoxycarbonyl-N-propyl)amino-5-[4,5-dihydropyridazin-3(2H)-on-6-yl]indane.

$IR^{neat}$ $\nu_{max}$ ($cm^{-1}$): 3200, 1680, 1660

Mass (m/z): 329 ($M^+$).

(3) To 13.16 g of the product obtained dissolved in 130 ml of chloroform was added 9 ml of iodotrimethylsilane, and the mixture was refluxed under heating for 2 hours. After cooling, aqueous ammonia was added to the mixture, the organic layer was collected by separation, washed with water and dried, and then the solvent was removed. The resulting crude crystals were recrystallized from acetone to obtain 7.78 g of 2-propylamino-5-[4,5-dihydropyridazin-3(2H)-on-6-yl]indane.

m.p.: 146° to 148° C.

(4) The product obtained and n-butylsulfonyl chloride were treated in the same manner as in Example 2 to obtain 28.96 g of 2-(N-n-butylsulfonyl-N-propyl)amino-5-[4,5-dihydropyridazin-3(2H)-on-6-yl]indane.

m.p.: 137° to 139° C.

Example 40

(1) 2-Aminoindane and 3-chloropropanesulfonyl chloride were treated in the same manner as in Example 31-(1) to obtain 2-(3-chloro)propanesulfonylaminoindane.

m.p.: 79° to 80° C.

(2) To 2.11 g of sodium hydride suspended in 50 ml of tetrahydrofuran was added dropwise 9.94 g of the above compound dissolved in 90 ml of tetrahydrofuran at room temperature. The temperature of the reaction mixture was raised to 50° to 55° C., and the mixture was stirred for 10 hours. The reaction mixture was poured into ice water and extracted with ethyl acetate. After the organic layer was washed with water and dried, the solvent was removed. The residue was purified by silica gel column chromatography (eluted by ethyl acetate:hexane=1:2) to obtain 7.77 g of 2-(thiazolidin-1,1-dioxide-2-yl)indane.

m.p.: 101° to 102° C.

(3) The above compound was treated in the same manner as in Example 31-(2) to obtain 2-(thiazolidin-1,1-dioxide-2-yl)-5-(3-carboxypropionyl )indane, and the product obtained was treated with hydrazine hydrate in the same manner as in Example 31-(3) to obtain 2-(thiazolidin-1,1-dioxide-2-yl)-5-[4,5-dihydropyridazin-3(2H)-on-6-yl] indane.

m.p.: 210° to 212° C.

Example 41

2-Amino-5-[4,5-dihydropyridazin-3(2H)-on-6-yl]indane was treated with chloroethanesulfonyl chloride in the presence of two equivalent amounts of triethylamine in the same manner as in Example 2 to obtain 2-vinyl sulfonylamino-5-[4,5-dihydropyridazin-3(2H)-on-6-yl]indane.

m.p.: 168° to 170° C.

Example 42

2-Amino-5-[4,5-dihydropyridazin-3(2H)-on-6-yl]indane was treated with ethylenesulfonyl fluoride in the same manner as in Example 2 to obtain 2-(thiazetidin-1,1-dioxide-2-yl)-5-[4,5-dihydropyridazin-3(2H)-on-6-yl]indane.

m.p.: 206° to 209° C.

Example 43

To 1.0 g of 2-n-butylsulfonylamino-5-[4,5-dihydropyridazin-3(2H)-on-6-yl]indane dissolved in 15 ml of dimethylformamide was added 118 mg of 62.6% sodium hydride under ice cooling, and the mixture was stirred for 20 minutes. To the mixture was added 544 mg of propyl iodide dissolved in 5 ml of dimethyl formamide, and the mixture was stirred at room temperature overnight. The reaction mixture was poured into ice water and extracted with ethyl acetate, the extract was washed with water and dried, and then the solvent was removed. The residue was purified by silica gel column chromatography (eluted by chloroform:ethyl acetate=5:1) to obtain 690 mg of 2-(N-n-butylsulfonyl-N-propyl)amino-5-[4,5-dihydropyridazin-3(2H)-on-6-yl]indane. This compound had the same physical property values as those of the compound obtained in Example 39-(4).

Examples 44 to 52

By treating the corresponding starting compounds in the same manner as in Example 43, compounds shown in the following Table 3 were obtained.

TABLE 3

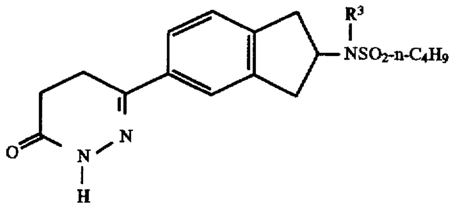

| Example No. | $R^3$ | Physical properties |
|---|---|---|
| 44 | $-CH_3$ | m.p. 152–154° C. |
| 45 | $-CH_2CH_3$ | m.p. 125–126° C. |
| 46 | $-CH_2CH=CH_2$ | m.p. 102–104° C. |
| 47 | $-CH_2CH(CH_3)_2$ | m.p. 138–140° C. |
| 48 | $-(CH_2)_3CH_3$ | MS (m/z): 405 ($M^+$)<br>IR (nujol)$cm^{-1}$:<br>3270, 1680, 1630 |
| 49 | 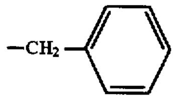 | m.p. 208–210° C. |
| 50 | 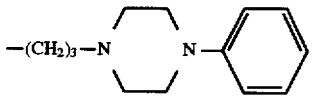 | m.p. 183–184° C.<br>(Fumarate) |
| 51 | 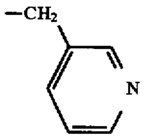 | m.p. 211–213° C. |
| 52 | 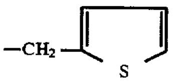 | m.p. 185–187° C. |

Example 53

2-n-Butyl sulfonylamino-5-[2-methyl-4,5-dihydropyridazin-3(2H)-on-6-yl]indane and methyl iodide were treated in the same manner as in Example 43 to obtain 2-(N-n-butylsulfonyl-N-methyl)amino- 5-[2-methyl-4,5-dihydropyridazin-3(2H)-on-6-yl]indane.

m.p.: 137° to 138° C.

Example 54

2-n-Butylsulfonylamino-5-{2-[3-(1-imidazolyl)propyl]-pyridazin-3(2H)-on-6-yl}indane and propyl iodide were treated in the same manner as in Example 43 to obtain 2-(N-n-butylsulfonyl-N-propyl)amino-5-{2-[3-(1-imidazolyl)-propyl]pyridazin-3(2H)-on-6-yl}indane.

$IR^{neat}$ $\nu_{max}$ ($cm^{-1}$): 1670

FAB-MS (m/z): 498 ($MH^+$).

Example 55

(1) In 70 ml of a 25% hydrogen bromide-acetic acid solution was suspended 8.02 g of 2-amino-5-[4,5-dihydropyridazin-3(2H)-on-6-yl]indane, and 2.96 g of dimethylsulfoxide sulfoxide was added thereto under ice cooling. The mixture was stirred at room temperature for 1.5 hours. Then, 140 ml of diethyl ether was added to the reaction mixture, and crystals precipitated were collected by filtration and recrystallized from methanol to obtain 8.55 g of 2-amino-5-[pyridazin-3(2H)-on-6-yl]indane hydrobromide m.p.: >300° C.

The product obtained was treated with sodium hydroxide to obtain 2-amino-5-[pyridazin-3(2H)-on-6-yl]indane.

m.p.: 228° to 229° C.

(2) In 50 ml of dimethylformamide were dissolved 1.14 g of 2-amino-5-[pyridazin-3(2H)-on-6-yl]indane and 0.8 g of triethyl amine, and 1.25 g of n-butanesulfonyl chloride was added thereto. The mixture was stirred at 50° C for 30 minutes and then stirred at room temperature overnight. The solvent was removed, water was added to the residue, and crystals precipitated were collected by filtration. The resulting crystals were recrystallized from methanol to obtain 1.27 g of 2-n-butylsulfonylamino-5-[pyridazin-3(2H)-on-6-yl] indane.

m.p.: 195° to 196° C.

Example 56

(1) 2-Propylamino-5-[4,5-dihydropyridazin-3(2H)-on-6-yl]indane was treated in the same manner as in Example 55-(1) to obtain 2-propylamino-5-[pyridazin-3(2H)-on-6-yl] -indane.

m.p.: 137° to 139° C.

(2) The product obtained and n-butylsulfonyl chloride were treated in the same manner as in Example 2 to obtain 2-(N-n-butylsulfonyl-N-propyl)amino-5-[pyridazin-3(2H)-on-6-yl]indane.

m.p.: 142° to 143° C.

Example 57

2-Propylamino-5-[pyridazin-3(2H)-on-6-yl]indane and chloroethanesulfonyl chloride were treated in the presence of two equivalent amounts of triethylamine in the same manner as in Example 2 to obtain 2-(N-vinylsulfonyl-N-propyl)amino-5-[pyridazin-3(2H)-on-6-yl]indane.

m.p.: 153° to 154° C.

Example 58

(1) 2-Propylamino-5-[4,5-dihydropyridazin-3(2H)-on-6-yl]indane and chloroethanesulfonyl chloride were treated in the presence of two equivalent amounts of triethylamine in the same manner as in Example 2 to obtain 2-(N-vinyl sulfonyl-N-propyl)amino-5-[4,5-dihydropyridazin-3(2H)-on-6-yl]indane.

m.p.: 135° to 136° C.

(2) In 10 ml of a 25% hydrogen bromide-acetic acid solution was suspended 1.16 g of the product obtained, and 0.25 ml of dimethylsulfoxide was added thereto. The mixture was stirred at room temperature for 1.5 hours. Hydrogen bromide-acetic acid were removed, and to the residue were added 30 ml of ethanol and then 10 ml of a 15% sodium methyl mercaptate aqueous solution. The mixture was stirred at 50° C. for 2.5 hours. Ethanol was removed, and ethyl acetate was added to the residue. The mixture was washed with water and dried, and then the solvent was removed. The resulting crude crystals were recrystallized from methanol no obtain 1.12 g of 2-[N-(2-methylthio) ethylsulfonyl-N-propyl]amino-5-[pyridazin-3(2H)-on-6-yl] indane.

m.p.: 130° to 131° C.

Example 59

2-Vinylsulfonylamino-5-[4,5-dihydropyridazin-3(2H)-on-6-yl]indane was treated in the same manner as in Example 58-(2) to obtain 2-(2-methylthio) ethylsulfonylamino-5-[pyridazin-3(2H)-on-6-yl]indane.

m.p.: 209° to 210° C.

Example 60

(1) In 100 ml of a 25% hydrogen bromide-acetic acid solution was suspended 17.44 g of 2-n-butylsulfonylamino-5-[4,5-dihydropyridazin-3(2H)-on-6-yl]indane, and 3.6 ml of dimethylsulfoxide was added thereto. The mixture was stirred at room temperature for 1 hour. Then, the reaction mixture was poured into ice water, and crystals precipitated were collected by filtration and recrystallized from methanol to obtain 14.60 g of 2-n-butylsulfonylamino-5-[pyridazin-3(2H)-on-6-yl]indane.

m.p.: 195° to 196° C.

Examples 61 to 85

By treating the corresponding starting compounds in the same manner as in Example 60, compounds shown in the following Tables 4 to 6 were obtained.

TABLE 4

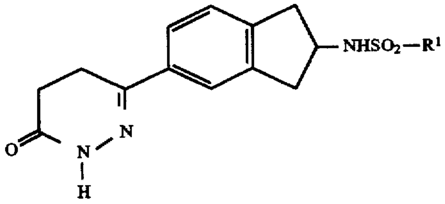

| Example No. | $R^1$ | Physical properties |
|---|---|---|
| 61 | $-CH_3$ | m.p. 228–229° C. |
| 62 | -n-$C_3H_7$ | m.p. 199–200° C. |
| 63 | $-CH(CH_3)_2$ | m.p. 213–215° C. |
| 64 | $-CH_2CH(CH_3)_2$ | m.p. 218–219° C. |
| 65 | -n-$C_5H_{11}$ | m.p. 201–202° C. |
| 66 | -n-$C_6H_{13}$ | m.p. 190–192° C. |
| 67 | -n-$C_7H_{15}$ | m.p. 186–187° C. |
| 68 | 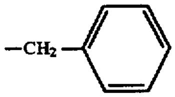 | m.p. 194–196° C. |
| 69 | 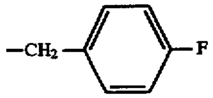 | m.p. 205–207° C. |
| 70 | 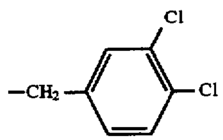 | m.p. 203–204° C. |
| 71 | 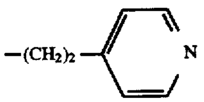 | m.p. 159–161° C. |
| 72 | 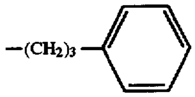 | m.p. 203–204° C. |

TABLE 4-continued

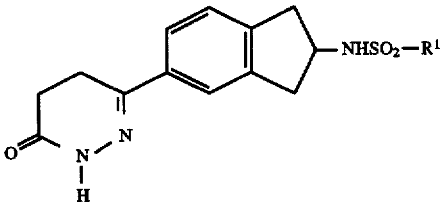

| Example No. | $R^1$ | Physical properties |
|---|---|---|
| 73 | 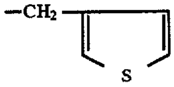 | m.p. 253–254° C. |
| 74 | 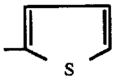 | m.p. 219–221° C. |
| 75 | 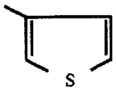 | m.p. 191–193° C. |
| 76 | $-CH{=}CH_2$ | m.p. 200–202° C. |
| 77 | $-CH_2CH_3$ | m.p. 220–221° C. |

TABLE 5

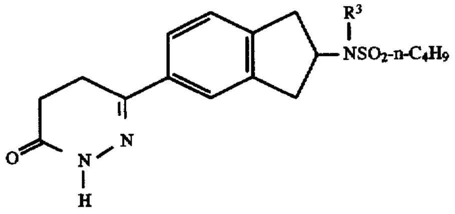

| Example No. | $R^3$ | Physical properties |
|---|---|---|
| 78 | $-CH_3$ | m.p. 168–169° C. |
| 79 | -n-$C_3H_7$ | m.p. 142–143° C. |
| 80 | 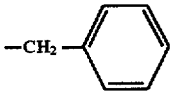 | m.p. 98–99° C. |
| 81 | 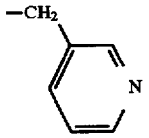 | m.p. 212–214° C. (hydrochloride) |
| 82 | 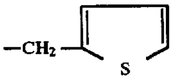 | m.p. 195–197° C. |

TABLE 6

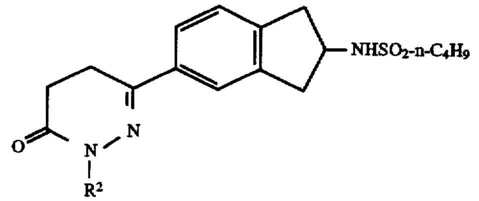

| Example No. | $R^2$ | Physical properties |
|---|---|---|
| 83 | $-CH_3$ | m.p. 152–153° C. |
| 84 | 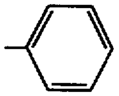 | m.p. 153–154° C. |
| 85 | 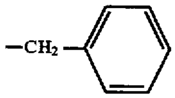 | m.p. 153–154° C. |

Example 86

(1) 2-Propylamino-5-[4,5-dihydropyridazin-3 (2H)-on-6-yl]indane and 2-thiophenesulfonyl chloride were treated in the same manner as in Example 2 to obtain 2-[N-propyl-N-(2-thiophenesulfonyl)]amino-5-[4,5-dihydropyridazin-3 (2H)-on-6-yl]indane.

m.p.: 129° to 130° C.

(2) The above compound was treated in the same manner as in Example 60 to obtain 2-[N-propyl-N-(2-thiophenesulfonyl)]amino-5-[pyridazin-3(2H)-on-6-yl] indane.

m.p.: 192° to 193° C.

Example 87

2-(Thiazolidin-1,1-dioxide-2-yl)-5-[4,5-dihydropyridazin-3(2H)-on-6-yl]indane was treated in the same manner as in Example 60 to obtain 2-(thiazolidin-1,1-dioxide-2-yl)-5-[pyridazin-3(2H)-on-6-yl]indane m.p.: 277° to 279° C. (decomposed).

Example 88

In 55 ml of water were dissolved 2.45 g of 2-n-butylsulfonylamino-5-[4,5-dihydropyridazin-3(2H)-on-6-yl]indane and 1.40 g of sodium hydroxide, and 2.66 g of sodium 3-nitrobenzenesulfonate was added thereto. The mixture was refluxed under heating for 5 hours. After cooling, the reaction mixture was made acidic with 10% hydrochloric acid and extracted with ethyl acetate, the extract was dried, and then the solvent was removed. The resulting crystals were recrystallized from methanol to obtain 1.62 g of 2-n-butylsulfonylamino-5-[pyridazin-3(2H)-on-6-yl]-indane.

m.p.: 195° to 196° C.

Examples 89 and 90

By treating the corresponding starting compounds in the same manner as in Example 88, compounds shown in the following Table 7 were obtained.

TABLE 7

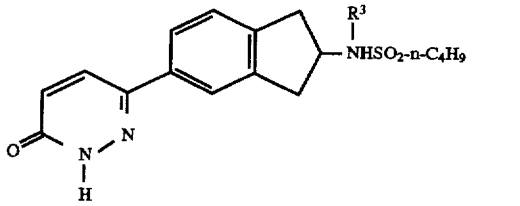

| Example No. | $R^3$ | Physical properties |
|---|---|---|
| 89 | $-CH_2CH=CH_2$ | m.p. 138–139° C. |
| 90 | 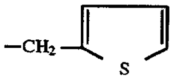 | m.p. 195–197° C. |

Example 91

To 1.0 g of 2-n-butylsulfonylamino-5-[pyridazin-3(2H)-on-6-yl]indane dissolved in 30 ml of dimethylformamide were added 828 mg of potassium carbonate and 547 mg of benzyl bromide, and the mixture was stirred at room temperature for 2 hours. Water was added to the reaction mixture, and crude crystals precipitated were collected by filtration, dried and then recrystallized from ethanol to obtain 1.15 g of 2-n-butyl sulfonylamino-5-[2-benzylpyridazin-3(2H)-on-6-yl]indane. This compound had the same physical property values as those of the compound obtained in Example 85.

Examples 92 to 105

By treating the corresponding starting compounds in the same manner as in Example 91, compounds shown in the following Table 8 were obtained.

TABLE 8

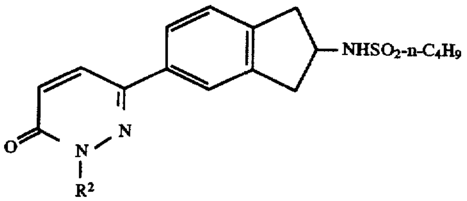

| Example No. | $R^2$ | Physical properties |
|---|---|---|
| 92 | 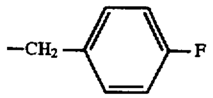 | m.p. 152–153° C. |
| 93 | 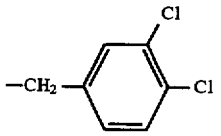 | m.p. 135–137° C. |

TABLE 8-continued

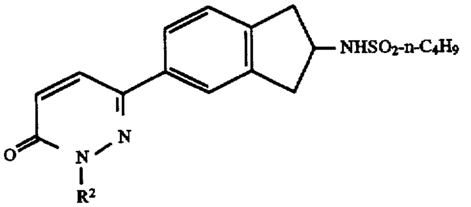

| Example No. | $R^2$ | Physical properties |
|---|---|---|
| 94 | 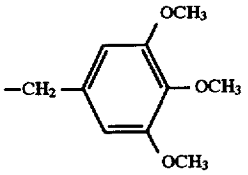 | m.p. 115–117° C. |
| 95 | 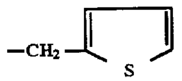 | m.p. 171–172° C. |
| 96 | 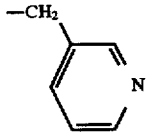 | m.p. 171–172° C. |
| 97 | $-CH_2CH{=}CH_2$ | FAB-MS (m/z): 388 ($MH^+$) $IR^{neat}$ $\nu_{max}$ ($cm^{-1}$): 3400–3100, 1660 |
| 98 | 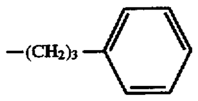 | FAB-MS (m/z): 466 ($MH^+$) $IR^{neat}$ $\nu_{max}$ ($cm^{-1}$): 3400–3100, 1665 |
| 99 | 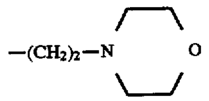 | m.p. 235–236° C. (hydrochloride) |
| 100 | $-(CH_2)_2N(CH_3)_2$ | m.p. 212–214° C. (hydrochloride) |
| 101 | 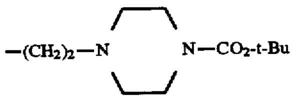 | FAB-MS (m/z): 574 ($MH^+$) $IR^{neat}$ $\nu_{max}$ ($cm^{-1}$): 3400–3100, 1700, 1660 |
| 102 | 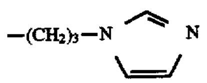 | m.p. 108–110° C. (hydrochloride) |
| 103 | $-CH_2COOC_2H_5$ | m.p. 82–84° C. |
| 104 | $-CH_2CN$ | m.p. 137–139° C. |
| 105 | $-CH_2CON(CH_3)_2$ | m.p. 82–83° C. (dec) |

Example 106

6 ml of trifluoroacetic anhydride was added dropwise to 3.3 g of 2-n-butylsulfonylamino-5-{2-[2-(4-t-butoxycarbonylpiperazin-1-yl)ethyl]pyridazin-3(2H)-on-6-yl}indane dissolved in 30 ml of dichloroethane, and the mixture was stirred at room temperature for 3 hours. To the reaction mixture was added a 1 0% sodium hydroxide aqueous solution, the organic layer was collected by separation, washed with water and dried, and then the solvent was removed. Hydrogen chloride-ethanol was added to the residue, and the resulting crude crystals were recrystallized from methanol to obtain 2.77 g of 2-n-butylsulfonylamino-5-{[2-(2-piperazin-1-yl)ethyl] pyridazin-3(2H)-on-6-yl}indane.dihydrochloride.

m.p.: 108° to 110° C.

Example 107

11.3 ml of a 1N sodium hydroxide aqueous solution was added dropwise under ice cooling to 3.25 g of 2-n-butylsulfonylamino-5-[2-ethoxycarbonylmethylpyridazin-3 (2H)-on-6-yl]indane suspended in 50 ml of methanol, and the mixture was stirred at room temperature for 5 hours. Methanol was removed, water was added to the residue, and the mixture was made acidic with 10% hydrochloric acid. Crystals precipitated were collected by filtration, washed with water and then recrystallized from ethanol-water to obtain 2.50 g of 2-n-butylsulfonylamino-5-[2-carboxymethylpyridazin-3(2H)-on-6-yl]indane.

m.p.: 186° to 188° C.

Example 108

To 2.23 g of 2-n-butylsulfonylamino-5-[2-cyanomethylpyridazin-3(2H)-on-6-yl]indane dissolved in 45 ml of dimethylformamide were added 1.8 g of sodium azide and 1.5 g of ammonium chloride, and the mixture was stirred at 95° C. for 3.5 hours. After cooling, water was added to the reaction mixture, and the mixture was made acidic with 10% hydrochloric acid. Crystals precipitated were collected by filtration, dried and then recrystallized from methanol to obtain 2.19 g of 2-n-butylsulfonylamino-5-[2-(5-tetrazolyl)methylpyridazin-3(2H)-on-6-yl]indane.

m.p.: 192° to 194° C.

Example 109

(1) 2-(N-n-butylsulfonyl-N-methyl)amino-5-[pyridazin-3 (2H)-on-6-yl]indane and ethyl bromoacetate were reacted in the same manner as in Example 91 to obtain 2-(N-n-butylsulfonyl-N-methyl)amino- 5-[2-ethoxycarbonylmethylpyridazin-3(2H)-on-6-yl]indane.

m.p.: 82° to 84° C.

(2 The product obtained was treated in the same manner as in Example 106 to obtain 2-(N-n-butylsulfonyl -N-methyl)amino-5-[2-carboxymethylpyridazin-3(2H)-on-6-yl]indane.

m.p.: 120° to 122° C.

Example 110

2-[N-n-Butylsulfonyl-N-(3-pyridyl)methyl]amino-5-[pyridazin-3(2H)-on-6-yl]indane and 3-picolyl chloride were treated in the same manner as in Example 91 to obtain 2-[N-n-butylsulfonyl-N-(3-pyridyl)methyl]amino-5-[2-(3-pyridyl)methylpyridazin-3(2H)-on-6-yl]indane.

m.p.: 162° to 164° C.

Example 111

To 10.3 g of 2-amino-6-[4,5-dihydropyridazin-3(2H)-on-6-yl]-1,2,3,4-tetrahydronaphthalene.hydroiodide suspended in 100 ml of 1,3-dimethyl-2-imidazolidinone was added 26.7 ml of triethylamine at room temperature, and the mixture was stirred for 30 minutes. Under ice cooling, to the mixture was added dropwise 12.6 ml of butanesulfonyl chloride, and the mixture was stirred at room temperature for 4 hours. To the mixture was added 40 ml of ethanol, and the mixture was further stirred for 30 minutes. Ethyl acetate was added to the reaction mixture, the organic layer was washed with water and dried, and then the solvent was removed. The resulting crude crystals were recrystallized from isopropanol to obtain 8.5 g of 2-n-butylsulfonylamino- 6-[4,5-dihydropyridazin-3(2H)-on-6-yl]-1,2,3,4-tetrahydronaphthalene.

m.p.: 185° to 187° C.

Examples 112 to 114

By treating the corresponding starting compounds in the same manner as in Example 111, compounds shown in the following Table 9 were obtained.

TABLE 9

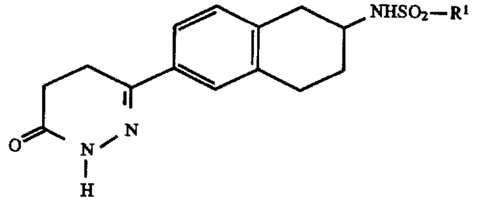

| Example No. | $R^1$ | Physical properties |
|---|---|---|
| 112 | $-C_2H_5$ | m.p. 157–158° C. |
| 113 | 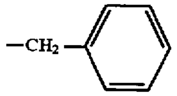 | m.p. 211–212° C. |
| 114 | 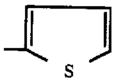 | m.p. 178–180° C. |

Example 115

2-n-Butylsulfonylamino-6-[4,5-dihydropyridazin-3(2H)-on-6-yl]-1,2,3,4-tetrahydronaphthalene was treated with dimethylsulfoxide-25% hydrogen bromide-acetic acid in the same manner as in Example 60 to obtain 2-n-butylsulfonylamino-6-[pyridazin-3(2H)-on-6-yl]-1,2,3,4-tetrahydronaphthalene.

m.p. 195° to 197° C.

Example 116

In 60 ml of acetone were suspended 2.40 g of the compound obtained in Example 114, 1.10 g of dimethylaminoethyl chloride hydrochloride and 3.70 g of potassium carbonate, and the mixture was refluxed under heating for 20 hours. Acetone was removed, the residue was dissolved in chloroform-water, and the organic layer was collected by separation. After the organic layer was washed with water and dried, the solvent was removed. The residue was treated with hydrogen chloride-ethanol to obtain hydrochloride, and the hydrochloride was recrystallized from a mixed solution of ethanol and ethyl ether to obtain 2.1 g of 2-n-butylsulfonylamino-6-[2-(2-dimethylaminoethyl)pyridazin-3(2H)-on-6-yl]-1,2,3,4-tetrahydronaphthalene.hydrochloride.

m.p.: 113° to 115° C. (decomposed).

Example 117

2-Amino-6-[4,5-dihydropyridazin-3(2H)-on-6-yl]-7-chloro-1,2,3,4-tetrahydronaphthalene.hydroiodide and butanesulfonyl chloride were treated in the same manner as in Example 111 to obtain 2-n-butylsulfonylamino-6-[4,5-dihydropyridazin-3(2H)-on-6-yl]-7-chloro-1,2,3,4-tetrahydronaphthalene.

m.p.: 183° to 185° C.

Example 118

(1) To 2.25 g of 5-[(2-methylphenyl)sulfonylamino]-4,5,6,7-tetrahydrobenzo[b]thiophene and 1.61 g of succinic anhydride suspended in 25 ml of dichloroethane was added 4.39 g of anhydrous aluminum chloride under ice cooling, and the mixture was stirred at room temperature for 3 hours. The reaction mixture was poured into ice water and extracted with ethyl acetate. After the resulting organic layer was washed and dried, the solvent was removed to obtain 3.47 g of 2-(3-carboxypropionyl)-5-[(2-methylphenyl)sulfonylamino]-4,5,6,7-tetrahydrobenzo[b]thiophene.

(2) To 3.47 g of the compound obtained above dissolved in 30 ml of ethanol was added 2.18 g of hydrazine monohydrate, and the mixture was refluxed under heating for 3 hours. After cooling, crystals precipitated were collected by filtration to obtain 2.31 g of 2-[4,5-dihydropyridazin-3(2H)-on-6-yl]-5-[(2-methylphenyl)sulfonylamino]-4,5,6,7-tetrahydrobenzo[b]thiophene.

m.p.: 204° to 206° C.

Examples 119 to 123

By treating the corresponding starting compounds in the same manner as in Example 118, compounds shown in the following Table 10 were obtained.

TABLE 10

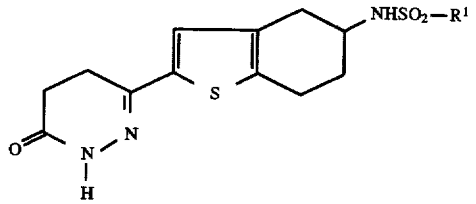

| Example No. | $R^1$ | Physical properties |
|---|---|---|
| 119 | 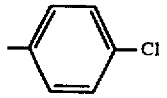 | m.p. 267–270° C. |
| 120 | 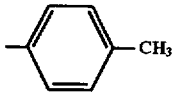 | m.p. 258–259° C. |
| 121 | 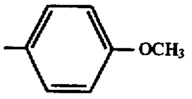 | m.p. 213.5–215.5° C. |
| 122 | 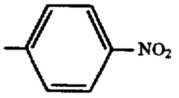 | m.p. >300° C. |
| 123 | $-n-C_4H_9$ | m.p. 191–192° C. |

Example 124

In 8 ml of a 25% hydrogen bromide-acetic acid solution was suspended 1.41 g of 2-[4,5-dihydropyridazin-3(2H)-on- 6-yl]-5-[(2-methylphenyl)sulfonylamino]-4,5,6,7-tetrahydrobenzo-[b]thiophene, and 0.25 ml of dimethylsulfoxide was added thereto. The mixture was stirred at room temperature for 2 hours. Then, diisopropyl ether was added to the reaction mixture, and crystals precipitated were collected by filtration to obtain 1.00 g of 2-[pyridazin-3(2H)-on-6-yl]-5-[(2-methylphenyl)sulfonylamino]-4,5,6,7-tetrahydrobenzo[b]thiophene.

m.p.: 242° to 247° C.

Examples 125 to 129

By treating the corresponding starting compounds in the same manner as in Example 124, compounds shown in the following Table 11 were obtained.

TABLE 11

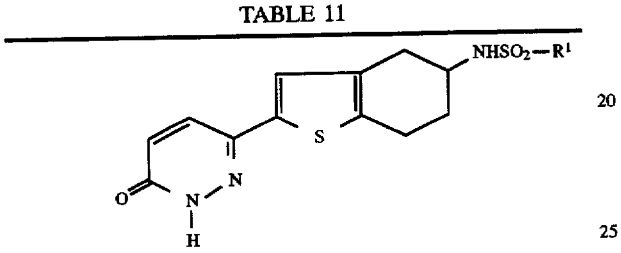

| Example No. | $R^1$ | Physical properties |
|---|---|---|
| 125 | 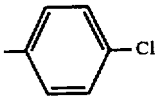 | m.p. 297.5–300° C. (dec) |
| 126 | 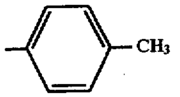 | m.p. 292–293° C. (dec) |
| 127 | 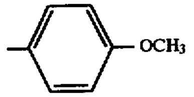 | m.p. 247–248° C. (dec) |
| 128 | 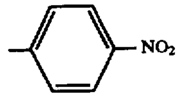 | m.p. 294–298° C. (dec) |
| 129 | $-n-C_4H_9$ | m.p. 230.5–231.5° C. |

Example 130

To 1.34 g of 2-[4,5-dihydropyridazin-3(2H)-on-6-yl]-5-amino-4,5,6,7-tetrahydrobenzo[b]thiophene.hydroiodide and 1.2 ml of triethylamine dissolved in 20 ml of 1,3-dimethyl-2-imidazolidinone was added 765 mg of benzenesulfonyl chloride, and the mixture was stirred at room temperature for 1 hour. The reaction mixture was poured into ice water and extracted with ethyl acetate. After the organic layer was washed and dried, the solvent was removed. The resulting crystals were recrystallized from nitromethane to obtain 1.22 g of 2-[4,5-dihydropyridazin-3(2H)-on-6-yl]-5-(phenylsulfonylamino)-4,5,6,7-tetrahydrobenzo[b]thiophene.

m.p.: 212° to 213° C.

Example 131

(1) In 10 ml of methanol was dissolved 1.01 g of 2-[4,5-dihydropyridazin-3(2H)-on-6-yl]-6-methoxycarbonylamino-4,5,6,7-tetrahydrobenzo[b]

thiophene, and 560 mg of potassium hydroxide dissolved in 5 ml of water was added thereto. The mixture was stirred at room temperature for 3 hours. Methanol was removed from the reaction mixture, the residue was extracted with ethyl acetate and dried, and the the solvent was removed to obtain 0.5 g of 2-[4,5-dihydropyridazin-3(2H)-on-6-yl]-6-amino-4,5,6,7-tetrahydrobenzo-[b]thiophene as crystals.

(2) In a mixture of 15 ml of ethyl acetate and 10 ml of tetrahydrofuran was dissolved 0.5 g of the compound obtained above, and 1.54 g of potassium carbonate dissolved in 10 ml of water was added thereto. The mixture was stirred. Then, to the mixture was added 0.7 g of benzenesulfonyl chloride under ice cooling, and the mixture was stirred at room temperature for 1.5 hours. After the organic layer was collected by separation, washed and dried, the solvent was removed. The resulting crystals were recrystallized from tetrahydrofuran-isopropyl ether to obtain 0.52 g of 2-[4,5-dihydropyridazin-3(2H)-on-6-yl]-6-phenylsulfonylamino-4,5,6,7-tetrahydrobenzo[b]thiophene.

m.p.: 230° to 232° C.

Examples 132 and 133

By treating the corresponding starting compounds in the same manner as in Example 131, compounds shown in the following Table 12 were obtained.

TABLE 12

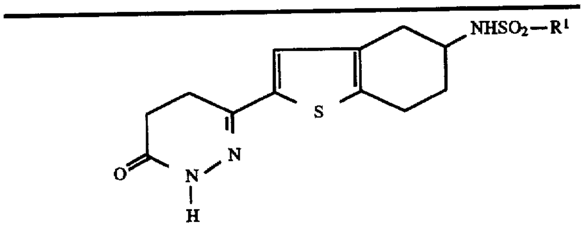

| Example No. | $R^1$ | Physical properties |
|---|---|---|
| 132 | 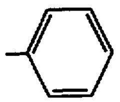 | m.p. 198–199° C. |
| 133 | $-n-C_4H_9$ | m.p. 164–165° C. |

Example 134

2-n-Propylsulfonylamino-5-[pyridazin-3(2H)-on-6-yl] indane and methyl iodide were reacted in the same manner as in Example 91 to obtain 2-n-propylsulfonylamino-5-[2-methylpyridazin-3(2H)-on-6-yl]indane.

m.p.: 182° to 183° C.

Reference example 1

(1) To 17.58 g of 2-methoxycarbonylaminosuccinic anhydride and 33.77 g of 4-chlorobenzene suspended in 150 ml of dichloroethane was added 33.40 g of anhydrous aluminum chloride under ice cooling, and the mixture was stirred at room temperature for 1 hour. Under ice cooling, to the mixture were added 100 ml of 10% hydrochloric acid and then 500 ml of ethyl acetate. After the organic layer was collected by separation, washed with water and dried, the solvent was removed. The resulting crude crystals were recrystallized from ethyl acetate to obtain 24.2 g of 3-carboxy-3-methoxycarbonylamino-4'-chloropropiophenone.

m.p.: 141° to 142° C.

(2) To 45.57 g of the above compound and 16.97 g of triethylamine dissolved in 400 ml of tetrahydrofuran was added dropwise 18.20 g of trimethylchlorosilane under ice cooling, and the mixture was stirred at room temperature for 1.5 hours. Triethylamine hydrochloride formed was removed, and tetrahydrofuran was removed. The residue was dissolved in 400 ml of dichloromethane, and 55.67 g of triethylsilane was added thereto. Then, to the mixture was added dropwise 90.9 g of titanium tetrachloride under ice cooling, and the mixture was stirred at room temperature for 18 hours. The reaction mixture was poured into conc. hydrochloric acid (50 ml)-ice and extracted with 1,000 ml of ethyl acetate. After the organic layer was collected by separation, washed with water and dried, the solvent was removed. The residue was purified by silica gel column chromatography (eluted by chloroform:methanol=100:1) to obtain 39.68 g of 1-chloro-4-(3-carboxy-3-methoxycarbonylaminopropyl)benzene.

m.p.: 113° to 114° C.

(3) To 10.0 g of the above compound dissolved in 200 ml of dichloromethane were added 3.9 ml of oxalyl chloride and one drop of dimethylformamide, and the mixture was stirred at room temperature for 30 minutes. To the mixture was added 12.4 g of anhydrous aluminum chloride under ice cooling, and the mixture was stirred at room temperature for 30 minutes. The reaction mixture was poured into ice water and extracted with ethyl acetate (1,000 ml). After the organic layer was washed with water and dried, the solvent was removed. The resulting crude crystals were recrystallized from a mixed solution of ethyl acetate and hexane to obtain 7.30 g of 1-oxo-2-methoxycarbonylamino-7-chloro-1,2,3,4-tetrahydronaphthalene.

m.p.: 126° to 127° C.

(4). To 13.47 g of the above compound dissolved in 40 ml of trifluoroacetic acid was added 24.1 g of triethylsilane. After the mixture was refluxed under heating for 3 hours, trifluoroacetic acid was removed. The residue was dissolved in ethyl acetate. After the solution was washed with water and dried, the solvent was removed. The resulting crude crystals were recrystallized from a mixed solution of ethyl acetate and hexane to obtain 10.52 g of 2-methoxycarbonylamino-7-chloro-1,2,3,4-tetrahydronaphthalene.

m.p.: 99° to 101° C.

(5) To 14.9 g of methyl hydrogen succinate dissolved in 180 ml of dichloromethane were added 10.3 ml of oxalyl chloride and one drop of dimethylformamide, and the mixture was stirred at room temperature for 3 hours. To the mixture were added 18.0 g of 2-methoxycarbonylamino-7-chloro-1,2,3,4-tetrahydronaphthalene obtained above and 40.0 g of anhydrous aluminum chloride under ice cooling, and the mixture was stirred at room temperature for 18 hours. The reaction mixture was poured into ice water, and the organic layer was collected by separation. After the organic layer was washed with water and dried, the solvent was removed. The resulting crude crystals were recrystallized from a mixed solution of ethyl acetate and hexane to obtain 24.3 g of 2-methoxycarbonylamino-6-(3-methoxycarbonylpropionyl)-7-chloro-1,2,3,4-tetrahydronaphthalene.

m.p.: 86° to 89° C.

(6) To 30.0 g of the above compound dissolved in 600 ml of dimethylformamide were added 60 ml of 90% formic acid and 7.5 g of 10% palladium-carbon, and the mixture was refluxed under heating for 15 hours. The residue was dissolved in ethyl acetate. After the solution was washed with water and dried, the solvent was removed to obtain 26.0 g 6f 2-methoxycarbonylamino-6-(3-methoxycarbonylpropionyl)-1,2,3,4-tetrahydronaphthalene.

m.p.: 109° to 111° C.

(7) To 26.0 g of the above compound dissolved in 260 ml of xylene were added 20.0 g of hydrazine monohydrate and 23 ml of acetic acid, and the mixture was refluxed under heating for 4 hours. Xylene was removed, and the resulting crude crystals were washed with water, dried and then recrystallized from isopropanol-diisopropyl ether to obtain 20.0 g of 2-methoxycarbonylamino-6-[4,5-dihydropyridazin-3(2H)-on-6-yl]-1,2,3,4-tetrahydronaphthalene.

m.p.: 197° to 198° C.

(8) To 9.5 g of the above compound suspended in 100 ml of chloroform was added 6.7 ml of iodotrimethylsilane, and the mixture was refluxed under heating for 1 hour while stirring. After cooling, to the mixture was added 3 ml of methanol, and the mixture was stirred for 20 minutes. Crystals precipitated were collected by filtration to obtain 11.5 g of 2-amino-6-[4,5-dihydropyridazin-3(2H)-on-6-yl]-1,2,3,4-tetrahydronaphthalene.hydroiodide.

m.p.: 228° to 230° C.

Reference example 2

(1) 2-Methoxycarbonylamino-6-(3-methoxycarbonylpropionyl)-7-chloro-1,2,3,4-tetrahydronaphthalene and hydrazine monohydrate were treated in the same manner as in Reference example 1-(7) to obtain 2-methoxycarbonylamino-6-[4,5-dihydropyridazin-3(2H)-on-6-yl]-7-chloro-2,3,4-tetrahydronaphthalene.

m.p.: 196° to 198°°C.

(2) The above compound and iodotrimethylsilane were treated in the same manner as in Reference example 1-(8) to obtain 11.5 g of 2-amino-6-[4,5-dihydropyridazin-3(2H)-on-6-yl]-7-chloro-1,2,3,4-tetrahydronaphthalene.hydroiodide.

m.p.: >250° C.

Reference example 3

To 2.00 g of 5-amino-4,5,6,7-tetrahydrobenzo[b]thiophene.hydrochloride and 2.40 g of triethylamine dissolved in 15 ml of methylene chloride was added dropwise 2.11 g of 2-methylbenzenesulfonyl chloride dissolved in 5 ml of methylene chloride under ice cooling, and the mixture was stirred for 1 hour. The reaction mixture was washed and dried, and then the solvent was removed. The resulting crystals were recrystallized from ethyl acetate-hexane to obtain 2.58 g of 5-[(2-methylphenyl)sulfonylamino]-4,5,6,7-tetrahydrobenzo[b]thiophene.

m.p.: 130° to 132° C.

Reference examples 4 to 8

By treating the corresponding starting compounds in the same manner as in Reference example 3, compounds shown in the following Table 13 were obtained.

TABLE 13

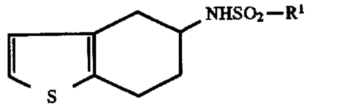

| Reference example No. | $R^1$ | Physical properties |
|---|---|---|
| 4 | 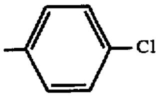 | m.p. 97.5–99.5° C. |
| 5 | 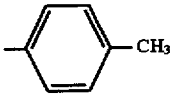 | m.p. 116–117° C. |
| 6 | 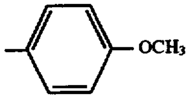 | m.p. 100–100.5° C. |
| 7 | 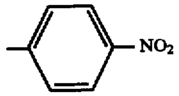 | m.p. 185–187° C. |
| 8 | $-n-C_4H_9$ | Oily product |

Reference example 9

(1) To 3.79 g of 5-amino-4,5,6,7-tetrahydrobenzo[b]thiophene.hydrochloride and 4.04 g of triethylamine dissolved in 30 ml of methylene chloride was added dropwise 1.89 g of methyl chlorocarbonate under ice cooling, and the mixture was stirred at room temperature for 2 hours. The reaction mixture was poured into ice water, the organic layer was collected by separation and dried, and then the solvent was removed. The resulting crystals were recrystallized from isopropyl ether to obtain 3.80 g of 5-methoxycarbonylamino-4,5,6,7-tetrahydrobenzo[b]thiophene.

m.p.: 108° to 109° C.

(2) To 5.00 g of the compound obtained above and 5.92 g of succinic anhydride suspended in 125 ml of dichloroethane was added 15.68 g of anhydrous aluminum chloride under ice cooling and stirring, and the mixture was stirred at room temperature overnight. The reaction mixture was poured into ice water and extracted with ethyl acetate. After the resulting organic layer was washed and dried, the solvent was removed to obtain 7.02 g of 2-(3-carboxypropionyl)-5-methoxycarbonylamino-4,5,6,7-tetrahydrobenzo[b]thiophene.

(3) To 7.02 g of the compound obtained above dissolved in 200 ml of ethanol was added 5.95 g of hydrazine monohydrate, and the mixture was refluxed under heating for 1.5 hours. The solvent was removed from the reaction mixture, and the resulting crystals were recrystallized from methanol to obtain 5.87 g of 2-[4,5-dihydropyridazin-3(2H)-on-6-yl]-5-methoxycarbonylamino-4,5,6,7-tetrahydrobenzo[b]thiophene.

m.p.: 205° to 206° C.

(4) To 2.35 g of the compound obtained above dissolved in 70 ml of chloroform was added dropwise 3.26 g of iodotrimethylsilane, and the mixture was refluxed under heating for 2 hours. After cooling, to the mixture was added 7 ml of methanol, and the mixture was stirred. Crystals precip- itated were collected by filtration to obtain 2.78 g of 2-[4,5-dihydropyridazin-3(2H)-on-6-yl]-5-amino-4,5,6,7-tetrahydrobenzo[b]thiophene.hydroiodide.

m.p.: >300° C.

Reference example 10

(1) 2-Chloro-5-amino-4,5,6,7-tetrahydrobenzo[b]thiophene.hydrochloride was treated in the same manner as in Reference example 9-(1) to obtain 2-chloro-5-methoxycarbonylamino-4,5,6,7-tetrahydrobenzo[b]thiophene.

m.p.: 120° to 121° C.

(2) To 2.51 g of the compound obtained above and 2.56 g of succinic anhydride suspended in 50 ml of dichloroethane was added 6.80 g of anhydrous aluminum chloride under ice cooling and stirring, and the mixture was stirred at room temperature for 7 hours. The reaction mixture was poured into ice water and extracted with ethyl acetate. After the organic layer was washed and dried, the solvent was removed to obtain 2.83 g of 2-chloro-3-(3-carboxypropionyl)-5-methoxycarbonylamino-4,5,6,7-tetrahydrobenzo[b]thiophene.

m.p.: 178° to 179° C.

(3) To 2.83 g of the compound obtained above and 3.5 ml of triethylamine dissolved in 50 ml of methanol was added 160 mg of 10% palladium-carbon, and the mixture was subjected to catalytic reduction at room temperature and atmospheric pressure of hydrogen for 2 hours. 10% Palladium-carbon was removed from the reaction mixture, and the solvent was removed. The residue was neutralized with 5% hydrochloric acid and then extracted with ethyl acetate. After the organic layer was washed and dried, the solvent was removed to obtain 2.45 g of 3-(3-carboxypropionyl)-5-methoxycarbonylamino-4,5,6,7-tetrahydrobenzo[b]thiophene.

m.p.: 187° to 188° C.

(4) To 2.45 g of the compound obtained above dissolved in 100 ml of ethanol was added 2.0 g of hydrazine monohydrate, and the mixture was refluxed under heating for 1 hour. The solvent was removed from the reaction mixture, and the resulting crystals were recrystallized from methanol to obtain 2.18 g of 3-[4,5-dihydropyridazin-3(2H)-on-6-yl]-5-methoxycarbonylamino-4,5,6,7-tetrahydrobenzo[b]thiophene.

m.p.: 223° to 224° C.

(5) The compound obtained above was treated in the same manner as in Reference example 9-(4) to obtain 3-[4,5-dihydropyridazin-3(2H)-on-6-yl]-5-amino-4,5,6,7-tetrahydrobenzo[b]thiophene.hydroiodide.

m.p.: >300° C.

Reference example 11

(1) 6-Amino-4,5,6,7-tetrahydrobenzo[b]thiophene.hydrochloride was treated in the same manner as in Reference example 9-(1) to obtain 6-methoxycarbonylamino-4,5,6,7-tetrahydrobenzo[b]thiophene.

m.p.: 156° to 157° C.

(2) To 1.06 g of the compound obtained above and 1.26 g of succinic anhydride suspended in 25 ml of dichloroethane was added 3.32 g of anhydrous aluminum chloride under ice cooling and stirring, and the mixture was stirred at room temperature for 1 hour. The reaction mixture was poured into ice water, the organic layer was collected by separation, washed and dried, and then the solvent was removed. The resulting crystals were recrystallized from tetrahydrofuran-isopropyl ether to obtain 1.10 g of 2-(3-carboxypropionyl)- 6-methoxycarbonylamino-4,5,6,7-tetrahydrobenzo[b]thiophene.

m.p.: 114° to 116° C.

(3) To 1.10 g of the compound obtained above dissolved in 10 ml of acetic acid was added 1.00 g of hydrazine monohydrate, and the mixture was refluxed under heating for 1 hour. The reaction mixture was poured into ice water and extracted with ethyl acetate. After the organic layer was washed and dried, the solvent was removed to obtain 1.01 g of 2-[4,5-dihydropyridazin-3(2H)-on-6-yl]-6-methoxycarbonylamino-4,5,6,7-tetrahydrobenzo[b]thiophene as a foamy product.

$IR^{neat}$ $\nu_{max}$ ($cm^{-1}$): 3280, 1690, 1660

Mass (m/z): 307 ($M^+$).

The desired pyridazinone derivatives (I) of the present invention and pharmaceutically acceptable salts thereof have excellent actions of protecting from endotoxin shock and excellent actions of curing nephritis so that they are useful as, for example, an agent for curing endotoxin shock which occurs in a patient seriously infected with gram-negative bacteria or an agent for curing nephritis. Further, the desired compound (I) of the present invention has low toxicity so that it can be a medicine having high safety.

We claim:

1. A pyridazinone compound represented by the formula (I-a):

(I-a)

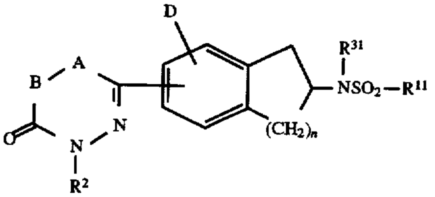

wherein, $R^2$ is a hydrogen atom or a lower alkyl group which may be substituted by a phenyl group;

$R^{11}$ is an alkyl group having 1 to 10 carbon atoms, a cycloalkyl group having 3 to 6 carbon atoms, or a lower alkenyl group; $R^{31}$ represents a hydrogen atom or a lower alkyl group; —A—B— is an ethylene group or a vinylene group, each of which may be substituted by 1 or 2 methyl groups or phenyl groups; n is 1; and D represents a hydrogen atom; or a pharmaceutically acceptable salt thereof.

2. The compound according to claim 1, wherein $R^{11}$ is an alkyl group having 1 to 10 carbon atoms; $R^2$ is a hydrogen atom or a lower alkyl group; $R^{31}$ represents a hydrogen atom; and —A—B— is an ethylene group or a vinylene group.

3. The compound according to claim 1, wherein $R^{11}$ is an alkyl group having 1 to 10 carbon atoms or a lower alkenyl group.

4. The compound according to claim 3, wherein $R^{11}$ is an alkyl group having 1 to 5 carbon atoms or a lower alkenyl group; $R^2$ is a hydrogen atom or a lower alkyl group; and $R^{31}$ is hydrogen atom or a lower alkyl group.

5. The compound according to claim 4, wherein $R^2$ is a hydrogen atom; and —A—B— is a vinylene group.

6. The compound according to claim 5, wherein $R^{11}$ is a lower alkenyl group; and $R^{31}$ is a lower alkyl group.

7. 2-(N-vinylsulfonyl-N-propyl)amino-5-[pyridazin-3(2H)-on-6-yl]indane.

8. The compound according to claim 1, wherein $R^{11}$ represents an alkyl group having 1 to 10 carbon atoms or a cycloalkyl group having 3 to 6 carbon atoms;

$R^{31}$ represents a hydrogen atom;

$R^2$ represents a hydrogen atom or a lower alkyl group that may be substituted by a phenyl group and —A—B— represents an ethylene group or a vinylene group each of which may be substituted by 1 or 2 methyl groups or phenyl groups;

n is 1; and

D is a hydrogen atom.

9. A pharmaceutical composition that comprises a pharmaceutically effective amount of the compound as set forth in claim 1 in an admixture with a conventional pharmaceutically acceptable carrier or diluent.

* * * * *

UNITED STATES PATENT AND TRADEMARK OFFICE

CERTIFICATE OF CORRECTION

PATENT NO. : 5,739,132
DATED : April 14, 1998
INVENTOR(S) : Akihiko ISHIDA et al.

It is certified that error appears in the above-identified patent and that said Letters Patent is hereby corrected as shown below:

On the Title Page:

Change Item [63] Related U.S. Application Data, to read as follows:

-- Continuation of Ser. No. 430,249, Apr. 28, 1994, abandoned, which is a continuation of Ser. No. 083,489, Jun. 30, 1993, abandoned--

Signed and Sealed this

Fifth Day of January, 1999

Attest:

*Attesting Officer*

*Acting Commissioner of Patents and Trademarks*